United States Patent [19]

Clark

[11] Patent Number: 4,886,798

[45] Date of Patent: * Dec. 12, 1989

[54] OPTICAL ISOMERS OF SULFONYLDECAHYDRO-8H-ISOQUINO-(2,1-G)(1,6) NAPHTHYRIDINES AND RELATED COMPOUNDS USEFUL AS $\alpha_2$-BLOCKERS

[75] Inventor: Robin D. Clark, Palo Alto, Calif.

[73] Assignee: Syntex (U.S.A.) Inc., Palo Alto, Calif.

[ * ] Notice: The portion of the term of this patent subsequent to Dec. 13, 2005 has been disclaimed.

[21] Appl. No.: 174,750

[22] Filed: Mar. 29, 1988

Related U.S. Application Data

[63] Continuation-in-part of Ser. No. 37,320, Apr. 13, 1987, abandoned.

[51] Int. Cl.[4] .................. A61K 31/47; C07D 455/03
[52] U.S. Cl. .................. 514/233.2; 514/255; 514/280; 514/285; 544/125; 544/361; 546/48; 546/70
[58] Field of Search .................. 546/48, 70; 544/125, 544/361; 514/280, 285, 233.2, 255

[56] References Cited

U.S. PATENT DOCUMENTS

| | | | |
|---|---|---|---|
| 3,953,598 | 4/1976 | Hall | 514/280 |
| 4,076,820 | 2/1978 | Archibald | 546/95 X |
| 4,353,911 | 10/1982 | Buzas | 546/70 X |
| 4,454,114 | 6/1986 | Ward et al. | 546/95 X |
| 4,550,114 | 10/1985 | White | 514/294 |
| 4,673,680 | 6/1987 | Pendleton | 514/285 |
| 4,690,928 | 9/1987 | Huff et al. | 514/285 |
| 4,791,108 | 12/1988 | Clark | 514/233.2 |

OTHER PUBLICATIONS

Szabo, et al., Investigation on the Chemistry of Berbans. 13-Azaberban Derivatives Via Reductive Cyclization of Delta-Oxonitriles, Nouv. J. Chim., vol. 4, No. 3, pp. 199-202 (1980).

Primary Examiner—Mukund J. Shah
Assistant Examiner—Diana G. Rivers
Attorney, Agent, or Firm—Brian Lewis; Tom M. Moran

[57] ABSTRACT

Compounds of the formula (1):

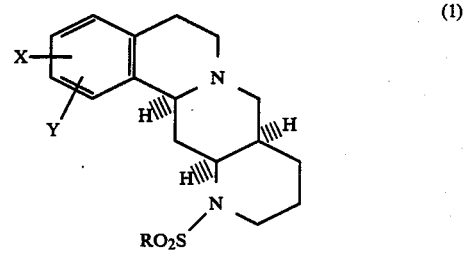

in which:

X and Y are independently hydrogen, hydroxy, lower alkyl, lower alkoxy or halo, or X and Y taken together is methylenedioxy or ethylene-1,2-dioxy, and R is lower alkyl, optionally substituted phenyl, —(CH$_2$)$_m$OR$^1$ or —NR$^1$R$^2$, wherein m is an integer of 1 to 6 and R$^1$ and R$^2$ are independently hydrogen or lower alkyl, or —NR$^1$R$^2$ taken together is a heterocycle of the formula:

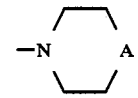

wherein A is —CH$_2$—, —NR$^1$— or oxygen; or a pharmaceutically acceptable salt thereof, are useful as selective $\alpha_2$-blockers.

21 Claims, No Drawings

OPTICAL ISOMERS OF SULFONYLDECAHYDRO-8H-ISOQUINO-(2,1-G)(1,6) NAPHTHYRIDINES AND RELATED COMPOUNDS USEFUL AS $\alpha_2$-BLOCKERS This is a Continuation-in-Part of U.S. patent application Ser. No. 037,320, filed Apr. 13, 1987, the complete disclosure of which is hereby incorporated by reference.

BACKGROUND OF THE INVENTION

Field of the Invention

The invention relates to optical isomers of various sulfonyldecahydro-8H-isoquino[2,1-g][1,6]naphthyridines which exhibit selective $\alpha_2$-blockade in mammals, and which, therefore, are useful as medicaments for the treatment of physiological conditions affected by such selective blockade. Such activities include, for example, lowering of blood pressure, amelioration of depression, inhibition of platelet aggregation, palliation of diabetes, alleviation of male impotence, weight-loss stimulation and lowering of intraoccular pressure. In addition, the compounds of formula (1) have been found to be useful for the treatment of irritable-bowel syndrome, cyclic mood disturbances in females and anxiolytic conditions.

Previous Disclosures

The novel compounds of this invention are optical isomers of various sulfonyldecahydro-8H-isoquino[2,1-g][1,6]naphthyridines, useful as selective $\alpha_2$-blockers. Compounds somewhat related to the novel compounds of this invention are described in U.S. Pat. Nos. 3,953,598, 4,353,911, 4,454,139 and 4,550,114, and in Nouveau J. Chim. 4(3), 199-202 (1980).

SUMMARY OF THE INVENTION

One aspect of the invention concerns novel compounds represented by the formula:

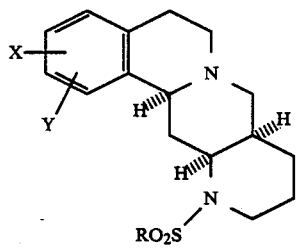
(1)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy, and R is lower alkyl of one to six carbon atoms, phenyl optionally substituted by one or two substituents chosen from halo or amino groups or lower alkyl or lower alkoxy groups of one to four carbon atoms, $-(CH_2)_m OR^1$ or $-NR^1R^2$ wherein m is an integer of 1 to 6 and $R^1$ and $R^2$ are independently hydrogen or lower alkyl, or $-NR^1R^2$ taken together is a heterocycle of the formula:

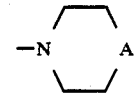

wherein A is $-CH_2-$, $-NR^1-$ or oxygen; or a pharmaceutically acceptable salt thereof.

Other aspects of the invention relate to the methods of preparation of compounds of formula (1) thereof, to pharmaceutical compositions containing such compounds in admixture with one or more pharmaceutically acceptable, non-toxic carriers, and to methods pertaining to their use.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like;

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated, for example phenyl optionally substituted by lower alkyl groups of one to four carbon atoms.

"Lower alkoxy" means the group $-OR$ wherein R is lower alkyl as herein defined.

"Halo" means fluoro, chloro, bromo and iodo.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The terms "$\alpha$ and $\beta$" indicate the specific stereochemical configuration of a substituent at an asymmetric carbon atom in a chemical structure as drawn. Thus "$\alpha$", denoted by a broken line, indicates that the group at the position in question is below the general plane of the molecule as drawn, and "$\beta$", denoted by a bold line, indicates that the group at the position in question is above the general plane of the molecule as drawn.

The term "(±)" is used to designate a racemic racemate as well as the individual (+) and (−) enantiomers and non-racemic mixtures thereof are included within the scope of this invention.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

"Diastereoisomers" are stereoisomers which are not mirror-images of each other.

"Epimers" are diastereoisomers which differ only in the configuration of one asymmetric center.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "disease state which is treatable with an $\alpha_2$-blocker" as used herein is intended to cover all disease states which are generally acknowledged in the literature to be usefully treated with $\alpha_2$-blockers in general, and those disease states which have been found to be usefully treated by the specific $\alpha_2$-blocker of our invention, the compound of formula (1). Such disease states include, but are not limited to, depression, anxiety, excessive platelet aggregation, diabetes, elevated intraocular pressure, male impotence, irritable bowel syndrome, hypertension, obesity and cyclic mood disturbances in females.

The absolute stereochemistry at carbons 8a, 12a and 13a is specified according to the Cahn-Ingold-Prelog R-S system. When the compound is a pure enantiomer, the stereochemistry at each chiral carbon is specified by either R or S. When a compound is a racemic mixture the stereochemistry at each chiral carbon is specified by either RS or SR by reference to a single enantiomer of the racemate. In this manner relative stereochemistry is conveyed unambiguously.

The compounds of the invention will be named using the numbering system shown below.

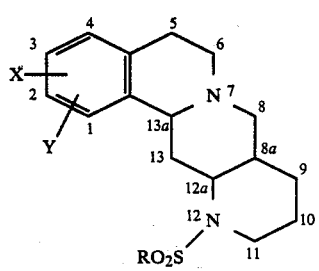

Following are examples of how representative compounds of formula (1) are named:

A compound of formula (1) wherein X is 3-methoxy, Y is hydrogen and R is methyl is named:
(8aR,12aS,13aS)-3-methoxy-12-methanesulfonyl-5,6,8a,9,10,11,12,12a,13,13a-decahydro-8H-isoquino[2,1-g][1,6]naphthyridine.

A compound of formula (1) wherein X and Y are hydrogen and R is 2-methylpropyl is named:
(8aR,12aS,13aS)-12-(2-methylpropanesulfonyl)-5,6,8a,9,10,11,12,12a,13,13a-decahydro-8H-isoquino[2,1-g][1,6]naphthyridine.

A compound of formula (1) wherein X and Y taken together is 2,3-methylenedioxy and R is dimethylamino, is named:
(8aR,12aS,13aS)-2,3-methylenedioxy-12-(N,N-dimethylaminosulfonyl)-5,6,8a,9,10,11,12,12a,13,13a-decahydro-8H-isoquino[2,1-g][1,6]naphthyridine.

Preferred Embodiments

Among the family of compounds of the present invention, a preferred group includes the compounds in which X and Y are independently hydrogen or lower alkoxy, or X and Y taken together is methylenedioxy, and R is lower alkyl, —(CH$_2$)$_m$OR$^1$ or —NR$^1$R$^2$. One preferred class within this group includes compounds in which X and Y taken together is methylenedioxy and R is lower alkyl, especially where R is methyl. A second preferred class within this group includes compounds in which X and Y are independently hydrogen or methoxy and R is methyl, dimethylamino or 2-methoxyethyl, especially where X is methoxy and Y is hydrogen.

At present, the preferred compounds are:
(8aR,12aS,13aS)-3-methoxy-12-methanesulfonyl-5,6,8a,9,10,11,12,12a,13,13a-decahydro-8H-isoquino[2,1-g][1,6]naphthyridine;
(8aR,12aS,13aS)-2,3-dimethoxy-12-methanesulfonyl-5,6,8a,9,10,11,12,12a,13,13a-decahydro-8H-isoquino-[2,1-g][1,6]naphthyridine;
(8aR,12aS,13aS)-2,3-methylenedioxy-12-methanesulfonyl-5,6,8a,9,10,11,12,12a,13,13a-decahydro-8H-isoquino-[2,1-g][1,6]naphthyridine hydrochloride;
(8aR,12aS,13aS)-12-methanesulfonyl-5,6,8a,9,10,11,12,-12a,13,13a-decahydro-8H-isoquino[2,1-g][1,6]naphthyridine;
(8aR,12aS,13aS)-12-(2-methoxyethanesulfonyl)-5,6,8a,9,10,11,12,12a,13,13a-decahydro-8H-isoquino[2,1-g][1,6]naphthyridine;
(8aR,12aS,13aS)-3-methoxy-12-(2-methoxyethanesulfonyl)-5,6,8a,9,10,11,12,12a,13,13a-decahydro-8H-isoquino[2,1-g][1,6]naphthyridine; and
(8aR,12aS,13aS)-3-methoxy-12-N,N-dimethylaminosulfonyl-5,6,8a,9,10,11,12,12a,13,13a-decahydro-8H-isoquino[2,1-g][1,6]naphthyridine.

Methods of Preparation

The compounds of formula (1) are prepared from the intermediates of formula (XI), the preparation of which is illustrated below in Reaction Scheme I.

It should be understood that the structures (IV), (V) and (VI) illustrated in Reaction Scheme I are intended to represent racemic mixtures, although for the sake of clarity only one enantiomer is shown. However, the structures (VII), (VIII), (IX), (X), (XI) and (XII) are intended to represent the single stereoisomer that is depicted.

REACTION SCHEME I
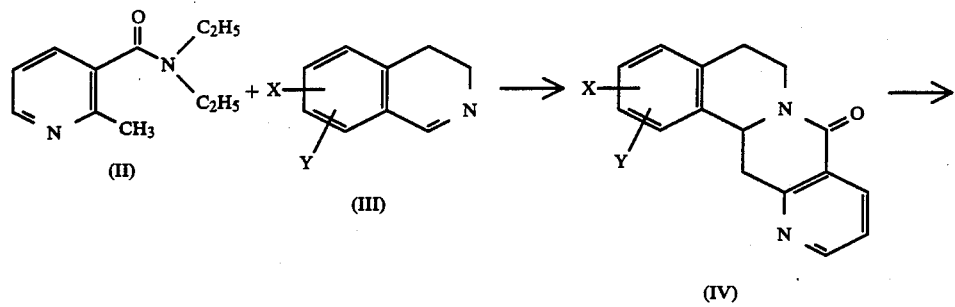
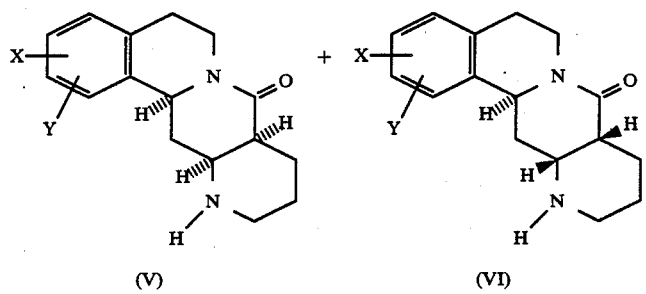
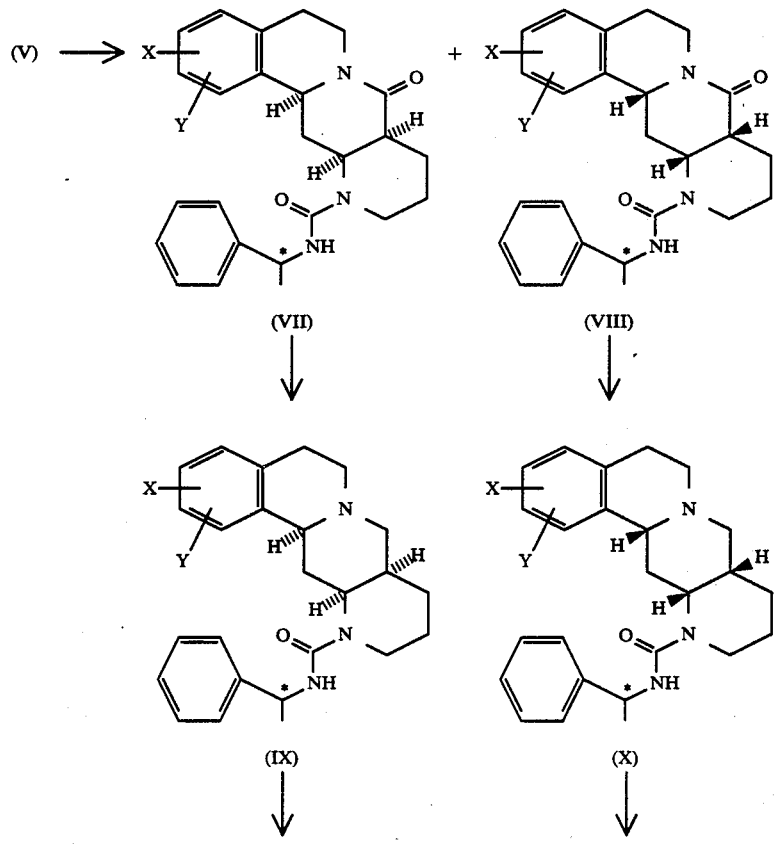

-continued
REACTION SCHEME I

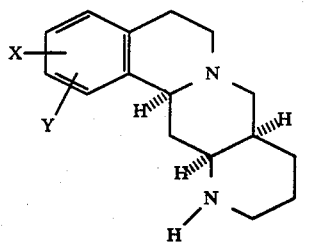

(XI)

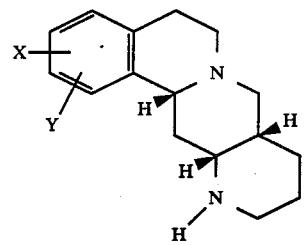

(XII)

The intermediate of formula (II), 2-methylnicotinic acid diethylamide, is prepared according to the method disclosed in Ber., 72B, 563 (1939). The intermediates of formula (III), optionally substituted dihydroisoquinolines, are prepared according to the method of Bischler-Napieralski, disclosed in Organic Reactions, Vol. VI, p 74 (1951), by the cyclization of formamidines of commercially available optionally substituted phenylethylamines. To prepare the compounds of formula (IV), the compounds of formula (II) and (III) are reacted together in the presence of a strong base, for example potassium t-butoxide, sodamide, sodium triphenylmethane, lithium diethylamide or preferably lithium diisopropylamide. The reaction is preferably carried out in an ethereal solvent, for example diethyl ether, dimethoxyethane, dioxane or tetrahydrofuran, at a temperature of about 0° C. to −50° C., preferably at about −10° C. to −40° C., for about 30 minutes to 4 hours. For example, diisopropylamine is dissolved in an ethereal solvent, preferably tetrahydrofuran, and cooled to a temperature of about −20° to −80° C., preferably about −65° C. To the cooled solution about 1 molar equivalent of an alkyl lithium, preferably 1.6M n-butyllithium, is added. To this cold solution is added a mixture of about 1 molar equivalent of the compound of formula (II) and about 1 molar equivalent of the compound of formula (III) in an ethereal solvent, preferably tetrahydrofuran. The reaction mixture is allowed to warm to about −10° to −40° C., preferably about −20° C., over a period of about 1 hour, and the reaction then quenched with an acid, preferably hydrochloric acid. The product of formula (IV), a (±)−5,6,13,13a-tetrahydroisoquino[2,1-g][1,6]naphthyridine-8-one hydrochloride, is isolated and purified by conventional means, preferably recrystallization of an acid salt.

The compound of formula (IV), preferably as the free base, is then hydrogenated with a suitable heterogeneous catalyst, for example palladium on carbon, platinum oxide or preferably rhodium on alumina, to give a mixture of the diastereoisomers of formula (V) and (VI). For example, for every gram of the compound of formula (III) in a solution of acetic acid is added from 0.1 to 0.6 g, preferably about 0.25 g, of 5% rhodium on alumina catalyst and the mixture hydrogenated at a pressure of about 25–80 psi, preferably about 50 psi. The reaction is conducted at a temperature of about 0° to 50° C., preferably about 25° C., for about 24–72 hours, preferably about 42 hours. When the reaction is substantially complete, the mixture of compounds of formula (IV) and (V) is isolated by conventional means and the mixture chromatographed on silica gel, eluting with a suitable solvent mixture, for example 5–20% methanol in methylene chloride. The first component eluted is the compound of formula (VI), followed by the compound of formula (V).

If desired, the racemic mixture of formula (V) may be separated into its two enantiomers at this stage of the synthesis. This may be accomplished by conventional resolution means; for example by separation (e.g. fractional crystallization) of the diastereomeric salts formed by the reaction of these compounds with optically active acids, at temperatures between 0° C. and the reflux temperature of the solvent employed for fractional crystallization. Exemplary of such optically active acids are the optically active forms of camphor-10-sulfonic acid, 2-bromo-camphor-10-sulfonic acid, camphoric acid, menthoxyacetic acid, tartaric acid, malic acid, mandelic acid, diacetyltartaric acid, pyrrolidine-5-carboxylic acid and the like. The preferred optically active acid is d-camphor-10-sulfonic acid, and the preferred solvent for recrystallization is ethyl acetate or a lower alkanol, for example methanol or ethanol, optionally with acetone as a cosolvent. The separated pure diastereomeric salts may then be cleaved by standard means, such as treatment with a base, to afford the respective enantiomers of the compound of formula (V). Conversion of the appropriate enantiomer of formula (V) to the compounds of formula (1) is then carried out as shown in U.S. patent application Ser. No. 037,320, filed Apr. 13, 1987, the relevant disclosures of which are hereby incorporated by reference.

Other methods of enantiomer separation include reacting the racemic amine with a chiral acid, for example 2R,3R−(+)-tartaric acid, using methods well known in the art, forming a mixture of two diastereoisomeric amides, which may be separated conventionally, for example by chromatography. Alternatively, reaction with a chiral chloroformate, for example R (−)-menthyl chloroformate, gives two diastereoisomeric carbamates, which may also be separated conventionally.

Racemic mixtures may also may be separated by chromatography on a chiral column. For example, on an $\alpha_1$-acid glycoprotein column eluting with a phosphate buffer composition.

Preferably, the compound of formula (V) is reacted with a chiral isocyanate to form a mixture of two diastereoisomeric ureas of formula (VII) and (VIII). For example, the compound of formula (V) is dissolved in an inert solvent, for example benzene, toluene, ethyl acetate, tetrahydrofuran, diethyl ether, chloroform or preferably dichloromethane, containing about 1 molar equivalent of a chiral isocyanate, preferably (R)−(+)-α-methylbenzylisocyanate. The reaction is conducted at a temperature of about 0° to 50° C., preferably about 25° C., for about 5 minutes to 4 hours, preferably about 30 minutes. When the reaction is substantially complete, the mixture of compounds of formula (VII) and (VIII) is isolated by conventional means. The two diastereoisomers are then preferably separated by chromatography on silica gel, especially medium pressure chromatography. The first component eluted is the compound of formula (VII), followed by the compound of formula (VIII).

The compounds of formula (VII) and (VIII) are then individually reduced to the compounds of formula (IX) and (X) with a suitable reducing agent, for example borane, triethyloxonium fluoroborate followed by sodium borohydride, sodium borohydride in the presence of a carboxylic acid, or preferably lithium aluminum hydride. For example, a solution of a compound of formula (VII) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1-10 hours, preferably about 3 hours. When the reaction is substantially complete, the compound of formula (IX) is separated and purified by conventional means. In a similar fashion, the compound of formula (VIII) is reduced to the compound of formula (X), and likewise separated and purified.

The compounds of formula (IX) and (X) are then individually hydrolyzed to the enantiomers of formula (XI) and (XII). Typically, the compound of formula (IX) or (X) is dissolved in a protic solvent, for example ethanol, propanol or preferably n-butanol, and added to a solution containing about 4 to 30 molar equivalents, preferably about 10 molar equivalents, of sodium dissolved in the same solvent. The mixture is refluxed for about 1-10 hours, preferably about 4 hours. When the reaction is substantially complete, the compound of formula (XI) is separated and purified by conventional means, preferably chromatography. In a similar fashion, the compound of formula (X) is hydrolyzed to the compound of formula (XII), and likewise separated and purified.

It should be noted that separation into optical isomers which is described above for the separation of the two enantiomers represented by the formula (V) may alternatively be carried out during the subsequent step, by the same procedures as shown above. That is, the compound of formula (V) could first be reduced with, for example, lithium aluminum hydride as shown above to a racemic mixture of the compounds represented by the formulas (XI) and (XII), and this racemic mixture similarly separated into its two enantiomers by the methods described supra.

Compounds of Formula (1)

Compounds of formula (1) are prepared from the compounds of formula (XI) as depicted in Reaction Sequence II below.

REACTION SCHEME II (XI) ⟶ 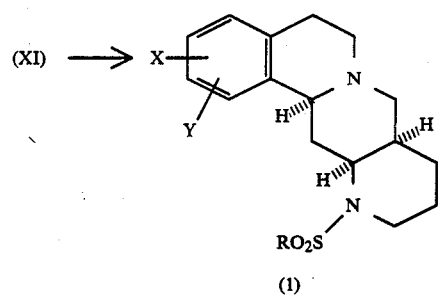

(1)

Similarly, the opposite enantiomer of formula (3) is obtained if the intermediate of formula (XII) is reacted as shown in Reaction Scheme II, i.e.:

(XII) ⟶ 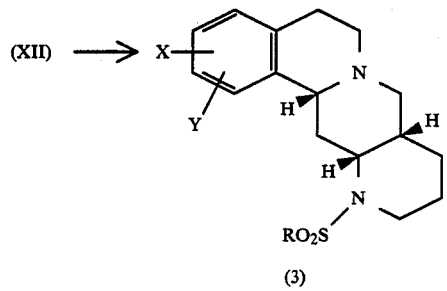

(3)

The compounds of formula (1) are prepared by reacting the compound of formula (XI) with a substituted sulfonyl halide of the formula $ZSO_2R$, where Z is chlorine or bromine and R is as defined above. The sulfonyl halides of formula $ZSO_2R$ are either commercially available from, inter alia, Aldrich Chemical Co., or may be prepared according to the method of Zeigler and Sprague, disclosed in J. Org. Chem., Vol 16, p 621 (1951).

For example, to prepare the compound of formula (1) the compound of formula (XI) is dissolved in an inert organic solvent, such as benzene, toluene, ethyl acetate, tetrahydrofuran, diethyl ether, chloroform or preferably dichloromethane, containing from 1-10 molar equivalents, preferably about 2 molar equivalents, of an inorganic base such as sodium carbonate, potassium bicarbonate or the like, or preferably a tertiary organic base, such as pyridine, N-methylpiperidine and the like, preferably triethylamine. The mixture is cooled to about −10° to 10° C., preferably about 0° C., and about 1-4 molar equivalents, preferably about 1.25 molar equivalents, of the appropriately substituted sulfonyl halide of formula $ZSO_2R$ added and the mixture stirred for about 30 minutes to 4 hours, preferably about 1 hour at a temperature of about 10° to 40° C., preferably about 25° C. An inert solvent, preferably diethyl ether, is then added, and the compound of formula (1) separated and purified by conventional means, for example recrystallization of an acid salt. If it is desired to prepare the compound of the formula (3) the compound of formula (XII) is reacted in the same manner as (XI) above, and likewise separated and purified.

It should be noted that separation into optical isomers may alternatively be carried out at this stage. That is, the racemic compound represented by a mixture of the compounds of formula (1) and (3), which would be obtained if no previous separation of optical isomers had been carried out (i.e. if the compounds of formula (XI) and (XII) had been reacted as a racemic mixture), could be separated into its two enantiomers by conventional resolution means, for example by separation (e.g. fractional crystallization) of the diastereomeric salts formed by the reaction of these compounds with optically active acids, or any of the methods described above, especially separation by chromatography on a chiral column. For example, separation of the enantiomers of formula (1) and (3) may be carried out on an $\alpha_1$-acid glycoprotein column eluting with a phosphate buffer composition.

An alternative preparation of the compound of formula (1) is shown in Reaction Scheme III below.

REACTION SCHEME III

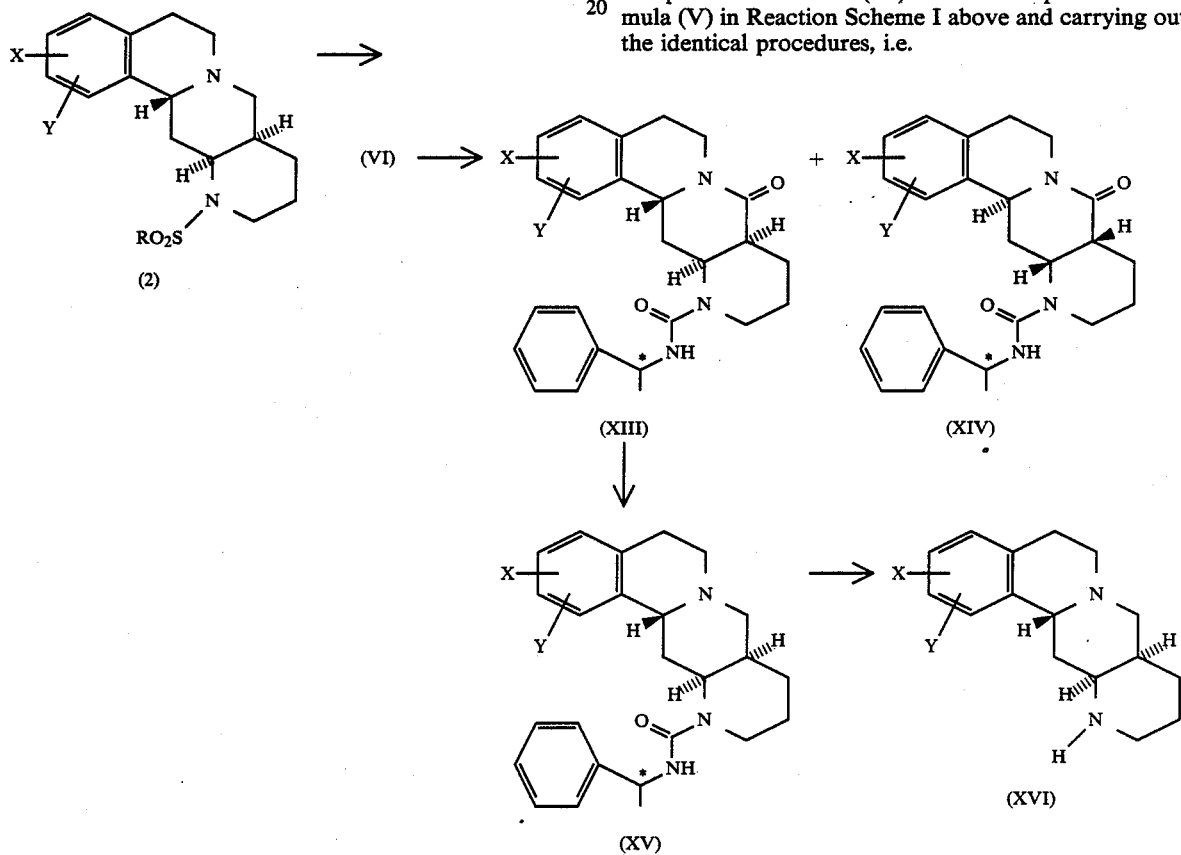

-continued
REACTION SCHEME III

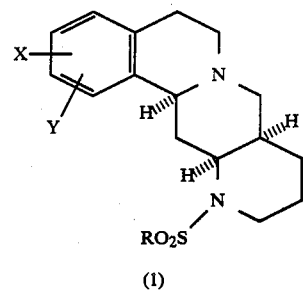

In this procedure, the compound of formula (2) is converted to the compound of formula (1). The compound of formula (2) is obtained by substituting the compound of formula (VI) for the compound of formula (V) in Reaction Scheme I above and carrying out the identical procedures, i.e.

Reacting the product of formula (XVI) thus obtained with a sulfonyl halide as shown in Reaction Scheme II gives a compound of the formula (2). If the isomers of formula (XIII) and (XIV) are not separated, a racemic mixture of the compound of formula (2) and its enantiomer is obtained, which may be separated into the individual enantiomers by the procedures shown in Reaction Schemes I and II above.

Typically, the compound of formula (2) is oxidized to a compound of formula (1) with about 1–10 molar equivalents, preferably about 4 molar equivalents, of an oxidizing agent. Representative oxidizing agents are iodine pentafluoride, Hg(II) salts, Pb(IV) salts, Ni(I) salts, Ag(II) salts, N-bromo- and N-chlorosuccinimide, $Cl_2$ and the like. A preferred oxidizing agent is a mercuric salt, preferably mercuric acetate. The compound of formula (2) and mercuric acetate are combined in acetic acid containing from about 5%–50%, preferably about 10%, of water and the mixture heated at a temperature of about 70° C. to the reflux temperature, preferably about 105° C., for about 30 minutes to 4 hours, preferably about 1 hour. After filtering, hydrogen sulfide is passed through, followed by refiltering and removal of the solvent from the filtrate. The residue is then dissolved in a protic solvent, preferably ethanol, the solution cooled to a temperature of about 0° to −40° C., preferably about −20° C., and treated with about 1 to 10 molar equivalents, preferably about 4 molar equivalents, of sodium borohydride. When the reaction is substantially complete the compound of formula (1) is isolated by conventional means, for example chromatography.

Alternatively, the conversion of a compound of formula (2) to (1) may be carried out by dissolving the compound of formula (2) in an inert solvent, preferably chloroform, at a temperature of about −20° to 10° C., preferably about 0° C., and treated with about 0.9 to 2 molar equivalents, preferably about 1.4 molar equivalents, of an oxidizing agent such as peracetic acid, perbenzoic acid or preferably metachloroperbenzoic acid, for about 10 minutes to 4 hours, preferably about 30 minutes, followed by about 20 minutes at room temperature. The reaction mixture is then recooled to about −20° to 10° C., preferably about 0 ° C., and treated with about 1 to 20 molar equivalents, preferably about 5.5 molar equivalents, of trifluoroacetic anhydride. The reaction is carried out at a temperature of about 10° to 30° C., preferably about 20° C., for about 5 minutes to about 2 hours, preferably about 30 minutes. The solvent is then removed under reduced pressure, and a protic solvent added, preferably ethanol. An excess of a reducing agent, preferably sodium borohydride, is then added slowly at a temperature of about −10° to 20° C., preferably about 0° C., until the solution becomes basic. When the reaction is substantially complete the compound of formula (1) is isolated by conventional means, for example chromatography or preferably recrystallization.

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures may be evaporated to a dryness, and the salts can be further purified by conventional methods such as those listed above.

Salts of Compounds of Formula (1)

The compounds of formula (1) may be converted to a corresponding acid addition salt by virtue of the presence of the tertiary nitrogen atom.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of formula (1) may be decomposed to the corresponding free bases by treatment with at least a stoichiometric amount of a suitable base such as sodium or potassium hydroxide, potassium carbonate, sodium bicarbonate, ammonia, and the like.

Utility and Administration

The compounds of formula (1) and the pharmaceutically acceptable acid addition salts thereof have been found to possess valuable pharmacological properties in the central nervous system and, in particular, have been shown to selectively block $\alpha_2$-receptors in standard laboratory tests. Accordingly these compounds and pharmaceutically acceptable compositions containing them are useful in the regulation of physiological phenomena related to $\alpha_2$-receptors, including lowering of blood pressure, amelioration of depression, inhibition of platelet aggregation, palliation of diabetes, alleviation of male impotence, weight-loss stimulation and lowering of intraocular pressure (useful in treating e.g. glaucoma). In addition, the compounds of formula (1) have been found to be useful for the treatment of irritable-bowel syndrome, cyclic mood disturbances in females and anxiolytic conditions.

In applying the compounds of this invention to treatment of conditions which are regulated by the CNS, administration of the active compounds and salts described herein can be via any of the accepted modes of administration for agents which relieve depression or affect the central nervous system including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of formula (1) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.001–1 mg/kg/day, preferably 0.01–0.5 mg/kg/day. For an average 70 kg human, this would amount to 0.07–70 mg per day, or preferably 0.7–35 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (1) or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 5–50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

For systemic administration via suppository, traditional binders and carriers include, e.g. polyalkalene glycols or triglycerides. Such suppositories may be formed from mixtures containing active ingredient in the range of 0.5%–10%; preferably 1–2%.

In applying the compounds of the invention to treatment of diseases or disorders of the eye which are associated with an abnormally high intraoccular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001% to 10%, most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6-8. Typical sterilants are phenyl mercuric acetate, thimerosal, chlorobutanol, and benzalconium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical occular composition could be administered at the rate of about 2–10 drops per day per eye of a 0.1% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

The following preparation and examples illustrate the invention but are not intended to limit its scope.

PREPARATION 1

Preparation of (±)-5,6,13,13a-Tetrahydroisoguino-[2,1-g][1,6]naphthyridin-8-one hydrochloride and Related Compounds of Formula (IV).

A. Diisopropylamine (28 ml) and 150 ml of tetrahydrofuran were cooled to −65° C. and 125 mL of 1.6M n-butyllithium was added. To the resulting solution was added a solution of 16.2 g of 3,4-dihydroisoquinoline and 38.4 g of 2-methylnicotinic acid diethylamide in tetrahydrofuran. The mixture was allowed to warm to −20° C. and 600 ml of 3N hydrochloric acid was then added followed by 200 ml of water. The mixture was basified with NH₄OH and extracted twice with ether. The ether extracts were combined, dried over anhydrous magnesium sulfate and evaporated to a residue, which was dissolved in methanol and acidified with anhydrous HCl in ether. Acetone (50 ml) was added and the mixture was allowed to stand overnight. The crystalline product was collected by filtration, yielding 34 g of (±)-5,6,13,13a-tetrahydroisoquino[2,1-g][1,6]naphthyridine-8-one hydrochloride, m.p. 220°–222° C.

An additional 7.5 g of the title compound as the free base was obtained by evaporation of the mother liquor followed by partitioning between ether and aqueous NH₄OH and silica gel chromatography of the residue obtained from evaporation of the ether, eluting with ethyl acetate, giving the free base, m.p. 72°–73° C.

B. Similarly, replacing 3,4-dihydroisoquinoline with the appropriate compound of formula (III) and following the procedure in paragraph A above, the following compounds of formula (IV) were prepared:

(±)-3-methoxy-5,6,13,13a-tetrahydroisoquino[2,1-g][1,6]naphthyridine-8-one hydrochloride, m.p. 244°–246° C.;

(±)-3-methoxy-5,6,13,13a-tetrahydroisoquino[2,1-g][1,6]naphthyridine-8-one, m.p. 115°–116° C.;

(±)-2,3-dimethoxy-5,6,13,13a-tetrahydroisoquino[2,1-g][1,6]naphthyridine-8-one hydrochloride, m.p. 238°–240° C.;

(±)-1,4-dimethoxy-5,6,13,13a-tetrahydroisoquino[2,1-g][1,6]naphthyridine-8-one hydrochloride;

(±)-2,3-methylenedioxy-5,6,13,13a-tetrahydroisoquino[2,1-g][1,6]naphthyridine-8-one, m.p. 177°–179° C.; and (±)-2,3-(ethylene-1,2-dioxy)-5,6,13,13a-tetrahydroisoquino[2,1-g][1,6]naphthyridine-8-one.

C. Similarly, replacing 3,4-dihydroisoquinoline with other compounds of formula (III) and following the procedure in paragraph A above, the following exemplary compounds of formula (IV) are prepared:

(±)-1-methyl-5,6,13,13a-tetrahydroisoquino[2,1-g][1,6]naphthyridine-8-one hydrochloride;

(±)-2-methyl-5,6,13,13a-tetrahydroisoquino[2,1-g][1,6]naphthyridine-8-one hydrochloride;

(±)-3-methyl-5,6,13,13a-tetrahydroisoquino[2,1-g][1,6]naphthyridine-8-one hydrochloride;

(±)-2,3-dimethyl-5,6,13,13a-tetrahydroisoquino[2,1-g][1,6]naphthyridine-8-one hydrochloride;

(±)-3-ethyl-5,6,13,13a-tetrahydroisoquino[2,1-g][1,6]naphthyridine-8-one hydrochloride;

(±)-3-isobutyl-5,6,13,13a-tetrahydroisoquino[2,1-g][1,6]naphthyridine-8-one hydrochloride;

(±)-3-n-hexyl-5,6,13,13a-tetrahydroisoquino[2,1-g][1,6]naphthyridine-8-one hydrochloride;

(±)-1-methoxy-5,6,13,13a-tetrahydroisoquino[2,1-g][1,6]naphthyridine-8-one hydrochloride;

(±)-2-methoxy-5,6,13,13a-tetrahydroisoquino[2,1-g][1,6]naphthyridine-8-one hydrochloride;

(±)-4-methoxy-5,6,13,13a-tetrahydroisoquino[2,1-g][1,6]naphthyridine-8-one hydrochloride;

(±)-3-methoxy-2-methyl-5,6,13,13a-tetrahydroisoquino[2,1-g][1,6]naphthyridine-8-one hydrochloride;

(±)-3-ethoxy-5,6,13,13a-tetrahydroisoquino[2,1-g][1,6]naphthyridine-8-one hydrochloride;

(±)-3-isopropoxy-5,6,13,13a-tetrahydroisoquino[2,1-g][1,6]naphthyridine-8-one hydrochloride;

(±)-3-isobutoxy-5,6,13,13a-tetrahydroisoquino[2,1-g][1,6]naphthyridine-8-one hydrochloride;

(±)-3-n-hexyloxy-5,6,13,13a-tetrahydroisoquino[2,1-g][1,6]naphthyridine-8-one hydrochloride;

(±)-3-hydroxy-5,6,13,13a-tetrahydroisoquino[2,1-g][1,6]naphthyridine-8-one hydrochloride;

(±)-2,3-dihydroxy-5,6,13,13a-tetrahydroisoquino[2,1-g][1,6]naphthyridine-8-one hydrochloride;

(±)-1,2-dimethoxy-5,6,13,13a-tetrahydroisoquino[2,1-g][1,6]naphthyridine-8-one hydrochloride;

(±)-1,4-dimethoxy-5,6,13,13a-tetrahydroisoquino[2,1-g][1,6]naphthyridine-8-one hydrochloride;

(±)-3,4-dimethoxy-5,6,13,13a-tetrahydroisoquino[2,1-g][1,6]naphthyridine-8-one hydrochloride;

(±)-2,3-diethoxy-5,6,13,13a-tetrahydroisoquino[2,1-g][1,6]naphthyridine-8-one hydrochloride;

(±)-2,3-di-n-butoxy-5,6,13,13a-tetrahydroisoquino[2,1-g][1,6]naphthyridine-8-one hydrochloride;

(±)-1,2-methylenedioxy-5,6,13,13a-tetrahydroisoquino[2,1-g][1,6]naphthyridine-8-one hydrochloride;

(±)-3,4-methylenedioxy-5,6,13,13a-tetrahydroisoquino[2,1-g][1,6]naphthyridine-8-one hydrochloride;

(±)-1-chloro-5,6,13,13a-tetrahydroisoquino[2,1-g][1,6]naphthyridine-8-one hydrochloride;

(±)-2-chloro-5,6,13,13a-tetrahydroisoquino[2,1-g][1,6]naphthyridine-8-one hydrochloride;

(±)-3-chloro-5,6,13,13a-tetrahydroisoquino[2,1-g][1,6]naphthyridine-8-one hydrochloride;

(±)-4-chloro-5,6,13,13a-tetrahydroisoquino[2,1-g][1,6]naphthyridine-8-one hydrochloride;

(±)-3-bromo-5,6,13,13a-tetrahydroisoquino[2,1-g][1,6]naphthyridine-8-one hydrochloride;

(±)-3-fluoro-5,6,13,13a-tetrahydroisoquino[2,1-g][1,6]naphthyridine-8-one hydrochloride; and (±)-2-fluoro-5,6,13,13a-tetrahydroisoquino[2,1-g][1,6]naphthyridine-8-one hydrochloride.

PREPARATION 2

Preparation of (±)-5,6,8aα,9,10,11,12,12aα,13,13aα-decahydroisoquino[2,1-g][1,6]naphthyridin-8-one (V) and (±)-5,6,8aβ,9,10,11,12,12aβ,13,13aα-Decahydroisoquino[2,1-g][1,6]naphthyridin-8-one (VI) and Related Compounds of Formula (V) and (VI).

A. A mixture of 30 g of (±)-5,6,13,13a-tetrahydroisoquino[2,1-g][1,6]naphthyridine-8-one, prepared as shown in Preparation 1 above, and 7.5 g of 5% Rh-Al₂O₃ in 300 ml of acetic acid was hydrogenated at 50 psi for 42 hours. The catalyst was removed by filtration and the filtrate was concentrated under reduced pressure. The residue was partitioned between methylene chloride and aqueous NH₄OH and the methylene chloride layer was separated and the solvent removed under reduced pressure. The residue was purified by silica gel chromatography, eluting with from 5-20% methanol in methylene chloride. The first component eluted was (±)-5,6,8aβ,9,10,11,12,12aβ,13,13aα-decahydroisoquino[2,1-g][1,6]naphthyridin-8-one (9.7 g), (VI), m.p. 105°-106° C. The second component eluted was (±)-5,6,8aα,9,10,11,12,12aα,13,13a-decahydroisoquino[2,1-g][1,6]naphthyridin-8-one (11.0 g), (V), m.p. 91°-92° C.

B. Similarly, replacing (±)-5,6,13,13a-tetrahydroisoquino[2,1-g][1,6]naphthyridine-8-one hydrochloride with the appropriate compound of formula (IV) and following the procedure in paragraph A above, the following compounds of formula (V) and (VI) were prepared:

(±)-3-methoxy-5,6,8aβ,9,10,11,12,12aβ,13,13aα-decahydroisoquino[2,1-g][1,6]naphthyridin-8-one; and (±)-3-methoxy-5,6,8aα,9,10,11,12,12aα,13,13aα-decahydroisoquino[2,1-g][1,6]naphthyridin-8-one, m.p. 118°-119° C.;

(±)-2,3-dimethoxy-5,6,8aβ,9,10,11,12,12aβ,13,13aβ-decahydroisoquino[2,1-g][1,6]naphthyridin-8-one; and (±)-2,3-dimethoxy-5,6,8aα,9,10,11,12,12aα,13,13aα-decahydroisoquino[2,1-g][1,6]naphthyridin-8-one;

(±)-1,4-dimethoxy-5,6,8aβ,9,10,11,12,12aβ,13,13aα-decahydroisoquino[2,1-g][1,6]naphthyridin-8-one; and (±)-1,4-dimethoxy-5,6,8aα,9,10,11,12,12aα,13,13aα-decahydroisoquino[2,1-g][1,6]naphthyridin-8-one;

(±)-2,3-methylenedioxy-5,6,8aβ,9,10,11,12,12aβ,13,13aα-decahydroisoquino[2,1-g][1,6]naphthyridin-8-one; and (±)-2,3-methylenedioxy-5,6,8aα,9,10,11,12,12aα,13,13aα-decahydroisoquino[2,1-g][1,6]naphthyridin-8-one;

(±)-2,3-(ethylene-1,2-dioxy)-5,6,8aβ,9,10,11,12,12aβ,13,13aα-decahydroisoquino[2,1-g][1,6]naphthyridin-8-one; and (±)-2,3-(ethylene-1,2-dioxy)-5,6,8aα,9,10,11,12,12aα,13,13aα-decahydroisoquino[2,1-g][1,6]naphthyridin-8-one.

C. Similarly, replacing (±)-5,6,13,13a-tetrahydroisoquino[2,1-g][1,6]naphthyridine-8-one hydrochloride with other compounds of formula (IV) and following the procedure in paragraph A above, the following exemplary compounds of formula (V) and (VI) are prepared:

(±)-1-methyl-5,6,8aβ,9,10,11,12,12aβ,13,13aα-decahydroisoquino[2,1-g][1,6]naphthyridin-8-one; and (±)-1-methyl-5,6,8aα,9,10,11,12,12aα,13,13aα-decahydroisoquino[2,1-g][1,6]naphthyridin-8-one;

(±)-2-methyl-5,6,8aβ,9,10,11,12,12aβ,13,13aα-decahydroisoquino[2,1-g][1,6]naphthyridin-8-one; and (±)-2-methyl-5,6,8aα,9,10,11,12,12aα,13,13aα-decahydroisoquino[2,1-g][1,6]naphthyridin-8-one;

(±)-3-methyl-5,6,8aβ,9,10,11,12,12aβ,13,13aα-decahydroisoquino[2,1-g][1,6]naphthyridin-8-one; and (±)-3-methyl-5,6,8aα,9,10,11,12,12aα,13,13aα-decahydroisoquino[2,1-g][1,6]naphthyridin-8-one;

(±)-2,3-dimethyl-5,6,8aβ,9,10,11,12,12aβ,13,13aα-decahydroisoquino[2,1-g][1,6]naphthyridin-8-one; and (±)-2,3-dimethyl-5,6,8aα,9,10,11,12,12aα,13,13aα-decahydroisoquino[2,1-g][1,6]naphthyridin-8-one;

(±)-3-ethyl-5,6,8aβ,9,10,12,12aβ,13,13aα-decahydroisoquino[2,1-g][1,6]naphthyridin-8-one; and (±)-3-ethyl-5,6,8aα,9,10,11,12,12aα,13,13aα-decahydroisoquino[2,1-g][1,6]naphthyridin-8-one;

(±)-3-isobutyl-5,6,8aβ,9,10,11,12,12aβ,13,13aα-decahydroisoquino[2,1-g][1,6]naphthyridin-8-one; and (±)-3-isobutyl-5,6,8aα,9,10,11,12,12aα,13,13aα-decahydroisoquino[2,1-g][1,6]naphthyridin-8-one;

(±)-3-n-hexyl-5,6,8aβ,9,10,11,12,12aβ,13,13aα-decahydroisoquino[2,1-g][1,6]naphthyridin-8-one; and (±)-3-n-hexyl-5,6,8aα,9,10,11,12,12aα,13,13aα-decahydroisoquino[2,1-g][1,6]naphthyridin-8-one;

(±)-1-methoxy-5,6,8aβ,9,10,11,12,12aα,13,13aα-decahydroisoquino[2,1-g][1,6]naphthyridin-8-one; and (±)-1-methoxy-5,6,8aα,9,10,11,12,12aα,13,13aα-decahydroisoquino[2,1-g][1,6]naphthyridin-8-one;

(±)-2-methoxy-5,6,8aβ,9,10,11,12,12aβ,13,13-aα-decahydroisoquino[2,1-g][1,6]naphthyridin-8-one; and (±)-2-methoxy-5,6,8aα,9,10,11,12,12aα,13,13aα-decahydroisoquino[2,1-g][1,6]naphthyridin-8-one;

(±)-4-methoxy-5,6,8aβ,9,10,11,12,12aβ,13,13aα-decahydroisoquino[2,1-g][1,6]naphthyridin-8-one; and (±)-4-methoxy-5,6,8aα,9,10,11,12,12aα,13,13aα-decahydroisoquino[2,1-g][1,6]naphthyridin-8-one;

(±)-3-methoxy-2-methyl-5,6,8aβ,9,10,11,12,12aβ,13,13aα-decahydroisoquino[2,1-g][1,6]naphthyridin-8-one; and (±)-3-methoxy-2-methyl-5,6,8aα,9,10,11,12,12aα,13,13aα-decahydroisoquino[2,1-g][1,6]naphthyridin-8-one;

(±)-3-ethoxy-5,6,8aβ,9,10,11,12,12aβ,13,13aα-decahydroisoquino[2,1-g][1,6]naphthyridin-8-one; and (±)-3-ethoxy-5,6,8aα,9,10,11,12,12aα,13,13aα-decahydroisoquino[2,1-g][1,6]naphthyridin-8-one;

(±)-3-isopropoxy-5,6,8aβ,9,10,11,12,12aβ,13,13aα-decahydroisoquino[2,1-g][1,6]naphthyridin-8-one; and (±)-3-isopropoxy-5,6,8aα,9,10,11,12,12aα,13,13aα-decahydroisoquino[2,1-g][1,6]naphthyridin-8-one;

(±)-3-isobutoxy-5,6,8aβ,9,10,11,12,12aβ,13,13aα-decahydroisoquino[2,1-g][1,6]naphthyridin-8-one; and (±)-3-isobutoxy-5,6,8aα,9,10,11,12,12aα,13,13aα-decahydroisoquino[2,1-g][1,6]naphthyridin-8-one;

(±)-3-n-hexyloxy-5,6,8aβ,9,10,11,12,12aβ,13,13aα-decahydroisoquino[2,1-g][1,6]naphthyridin-8-one; and (±)-3-n-hexyloxy-5,6,8aα,9,10,11,12,12aα,13,13aα-decahydroisoquino[2,1-g][1,6]naphthyridin-8-one;

(±)-3-hydroxy-5,6,8aβ,9,10,11,12,12aβ,13,13aα-decahydroisoquino[2,1-g][1,6]naphthyridin-8-one; and (±)-3-hydroxy-5,6,8aα,9,10,11,12,12aα,13,13aα-decahydroisoquino[2,1-g][1,6]naphthyridin-8-one;

(±)-2,3-dihydroxy-5,6,8aβ,9,10,11,12,12aβ,13,13aα-decahydroisoquino[2,1-g][1,6]naphthyridin-8-one; and (±)-2,3-dihydroxy-5,6,8aα,9,10,11,12,12aα,13,13aα-decahydroisoquino[2,1-g][1,6]naphthyridin-8-one;

(±)-1,2-dimethoxy-5,6,8aβ,9,10,11,12,12aβ,13,13aα-decahydroisoquino[2,1-g][1,6]naphthyridin-8-one; and (±)-1,2-dimethoxy-5,6,8aα,9,10,11,12,12aα,13,13aα-decahydroisoquino[2,1-g][1,6]naphthyridin-8-one;

(±)-1,4-dimethoxy-5,6,8aβ,9,10,11,12,12aβ,13,13aα-decahydroisoquino[2,1-g][1,6]naphthyridin-8-one; and (±)-1,4-dimethoxy-5,6,8aα,9,10,11,12,12aα,13,13aα-decahydroisoquino[2,1-g][1,6]naphthyridin-8-one;

(±)-3,4-dimethoxy-5,6,8aβ,9,10,11,12,12aβ,13,13aα-decahydroisoquino[2,1-g][1,6]naphthyridin-8-one; and (±)-3,4-dimethoxy-5,6,8aα,9,10,11,12,12aα,13,13aα-decahydroisoquino[2,1-g][1,6]naphthyridin-8-one;

(±)-2,3-diethoxy-5,6,8aβ,9,10,11,12,12aβ,13,13aα-decahydroisoquino[2,1-g][1,6]naphthyridin-8-one; and (±)-2,3-diethoxy-5,6,8aα,9,10,11,12,12aα,13,13aα-decahydroisoquino[2,1-g][1,6]naphthyridin-8-one;

(±)-2,3-di-n-butoxy-5,6,8aβ,9,10,11,12,12aβ,13,13aα-decahydroisoquino[2,1-g][1,6]naphthyridin-8-one; and (±)-2,3-di-n-butoxy-5,6,8aα,9,10,11,12,12aα,13,13aα-decahydroisoquino[2,1-g][1,6]naphthyridin-8-one;

(±)-1,2-methylenedioxy-5,6,8aβ,9,10,11,12,12aβ,13,13aα-decahydroisoquino[2,1-g][1,6]naphthyridin-8-one; and (±)-1,2-methylenedioxy-5,6,8aα,9,10,11,12,12aα,13,13aα-decahydroisoquino[2,1-g][1,6]naphthyridin-8-one;

(±)-2-chloro-5,6,8aβ,9,10,11,12,12aβ,13,13aα-decahydroisoquino[2,1-g][1,6]naphthyridin-8-one; and (±)-2-chloro-5,6,8aα,9,10,11,12,12aα,13,13aα-decahydroisoquino[2,1-g][1,6]naphthyridin-8-one;

(±)-3-chloro-5,6,8aβ,9,10,11,12,12aβ,13,13aα-decahydroisoquino[2,1-g][1,6]naphthyridin-8-one; and (±)-3-chloro-5,6,8aα,9,10,11,12,12aα,13,13aα-decahydroisoquino[2,1-g][1,6]naphthyridin-8-one;

(±)-4-chloro-5,6,8aβ,9,10,11,12,12aβ,13,13aα-decahydroisoquino[2,1-g][1,6]naphthyridin-8-one; and (±)-4-chloro-5,6,8aα,9,10,11,12,12aα,13,13aα-decahydroisoquino[2,1-g][1,6]naphthyridin-8-one;

(±)-3-bromo-5,6,8aβ,9,10,11,12,12aβ,13,13aα-decahydroisoquino[2,1-g][1,6]naphthyridin-8-one; and (±)-3-bromo-5,6,8aα,9,10,11,12,12aα,13,13aα-decahydroisoquino[2,1-g][1,6]naphthyridin-8-one;

(±)-3-fluoro-5,6,8aβ,9,10,11,12,12aβ,13,13aα-decahydroisoquino[2,1-g][1,6]naphthyridin-8-one; and (±)-3-fluoro-5,6,8aα,9,10,11,12,12aα,13,13aα-decahydroisoquino[2,1-g][1,6]naphthyridin-8-one;

(±)-2-fluoro-5,6,8aβ,9,10,11,12,12aβ,13,13aα-decahydroisoquino[2,1-g][1,6]naphthyridin-8-one; and (±)-2-fluoro-5,6,8aα,9,10,11,12,12aα,13,13aα-decahydroisoquino[2,1-g][1,6]naphthyridin-8-one;

PREPARATION 3

Preparation of
(8aS,12aS,13aS)-3-methoxy-12-(1-R-phenethylaminocarbonyl)-5,6,8a,9,10,11,12,12a,13,13a-decahydroisoquino[2,1-g][1,6]naphthyridin-8-one (VII) and
(8aR,12aR,13aR)-3-methoxy-12-(1-R-phenethylaminocarbonyl)-5,6,8a,9,10,11,12,12a,13,13a-decahydroisoquino[2,1-g][1,6]naphthyridin-8-one (VIII) and Related Compounds of Formula (VII), (VIII), (XIII) and (XIV)

A. A solution of 1.95 g of (±)-3-methoxy-5,6,8aα,9,10,11,12,12aα,13,13aαdecahydroisoquino[2,1-g][1,6]naphthyridin-8-one, a compound of formula (V), and 1.0 g of (R)-(+)-α-methylbenzyl isocyanate in 50 ml of methylene chloride was stirred at room temperature for 30 minutes. Solvent was then removed under reduced pressure, and the residue chromatographed on silica gel, using multiple medium pressure chromatography and eluting with 5% methanol in ethyl acetate. The first compound eluted was (8aS,12aS,13aS)-3-methoxy-12-(1-R-phenethylaminocarbonyl)-5,6,8a,9,10,11,12,-12a,13,13a-decahydroisoquino[2,1-g][1,6]naphthyridin-8-one, mp 198°-199° C., $[\alpha]_D^{25} = +36.5$ (CHCl$_3$) followed by (8aR,12aR,13aR)-3-methoxy-12-(1-R-phenethylaminocarbonyl)-5,6,8a,9,10,11,12,12a,13,13a-decahydroisoquino[2,1-g][1,6]naphthyridin-8-one, mp 220°-221° C., $[\alpha]_D^{25} = -11.4$ (CHCl$_3$).

B. Similarly, replacing (±)-3-methoxy-5,6,8aα,9,10,11,12,12aα,13,13aα-decahydroisoquino[2,1-g][1,6]naphthyridin-8-one with the appropriate compound of formula (V) and following the procedure in paragraph A above, the following compounds of formula (VII) and (VIII) were prepared:

(8aS,12aS,13aS)-12-(1-R-phenethylaminocarbonyl)-5,6,8a,9,10,11,12,12a,13,13a-decahydroisoquino[2,1-g][1,6]naphthyridin-8-one; and (8aR,12aR,13aR)-12-(1-R-phenethylaminocarbonyl)-5,6,8a,9,10,11,12,12a,13,13a-decahydroisoquino[2,1-g][1,6]naphthyridin-8-one;

(8aS,12aS,13aS)-2,3-methylenedioxy-12-(1-R-phenethylaminocarbonyl)-5,6,8a,9,10,11,12,12a,13,13a-decahydroisoquino[2,1-g][1,6]naphthyridin-8-one; and (8aR,12aR,13aR)-2,3-methylenedioxy-12-(1-R-phenethylaminocarbonyl)-5,6,8a,9,10,11,12,12a,-13,13a-decahydroisoquino[2,1-g][1,6]naphthyridin-8-one;

C. Similarly, replacing (±)-3-methoxy-5,6,8aα,9,10,11,12,12aα,13,13aα-decahydroisoquino[2,1-g][1,6]naphthyridin-8-one with the appropriate compound of formula (V) and following the procedure in paragraph A above, the following compounds of formula (VII) and (VIII) are prepared:

(8aS,12aS,13aS)-2,3-dimethoxy-12-(1-R-phenethylaminocarbonyl)-5,6,8a,9,10,11,12,12a,13,13a-decahydroisoquino[2,1-g][1,6]naphthyridin-8-one; and (8aR,12aR,13aR)-2,3-dimethoxy-12-(1-R-phenethylaminocarbonyl)-5,6,8a,9,10,11,12,12a,13,13a-decahydroisoquino[2,1-g][1,6]naphthyridin-8-one;

(8aS,12aS,13aS)-1,4-dimethoxy-12-(1-R-phenethylaminocarbonyl)-5,6,8a,9,10,11,12,12a,13,13a-decahydroisoquino[2,1-g][1,6]naphthyridin-8-one; and (8aR,12aR,13aR)-1,4-dimethoxy-12-(1-R-phenethylaminocarbonyl)-5,6,8a,9,10,11,12,12a,13,13a-decahydroisoquino[2,1-g][1,6]naphthyridin-8-one;

(8aS,12aS,13aS)-2,3-(ethylene-1,2-dioxy)-12-(1-R-phenethylaminocarbonyl)-5,6,8a,9,10,11,12,12a,13,-13a-decahydroisoquino[2,1-g][1,6]naphthyridin-8-one; and (8aR,12aR,13aR)-2,3-(ethylene-1,2-dioxy)-12-(1-R-phenethylaminocarbonyl)-5,6,8a,9,10,11,12,12a,13,-13a-decahydroisoquino[2,1-g][1,6]naphthyridin-8-one;

(8aS,12aS,13aS)-1-methyl-(1-R-phenethylaminocarbonyl)-5,6,8a,9,10,11,12,12a,13,13a-decahydroisoquino[2,1-g][1,6]naphthyridin-8-one; and (8aR,12aR,13aR)-1-methyl-(1-R-phenethylaminocarbonyl)-5,6,8a,9,10,11,12,12a,13,13a-decahydroisoquino[2,1-g][1,6]naphthyridin-8-one;

(8aS,12aS,13aS)-2-methyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2-methyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-methyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-methyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-2,3-dimethyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2,3-dimethyl-(1-R-phenethylaminocarbonyl)-5,6,8a,9,10,11,12,12a,13,13a-decahydroisoquino[2,1-g][1,6-]naphthyridin-8-one;
(8aS,12aS,13aS)-3-ethyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-ethyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-isobutyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-isobutyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-n-hexyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-n-hexyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-1-methoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-1-methoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-2-methoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2-methoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-4-methoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-4-methoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-methoxy-2-methyl-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-methoxy-2-methyl-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-ethoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-ethoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-isopropoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-isopropoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-isobutoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-isobutoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-n-hexyloxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-n-hexyloxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3-hydroxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3-hydroxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-2,3-dihydroxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2,3-dihydroxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-1,2-dimethoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-1,2-dimethoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-1,4-dimethoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-1,4-dimethoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-3,4-dimethoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-3,4-dimethoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-2,3-diethoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2,3-diethoxy-(1-R-phenethylaminocarbonyl)-5,6,8a,9,10,11,12,12a,13,13a-decahydroisoquino[2,1-g][1,6]naphthyridin-8-one;
(8aS,12aS,13aS)-2,3-di-n-butoxy-(1-R-phenethylaminocarbonyl)-5,6,8a,9,10,11,12,12a,13,13a-decahydroisoquino[2,1-g][1,6]naphthyridin-8-one; and
(8aR,12aR,13aR)-2,3-di-n-butoxy-(1-R-phenethylaminocarbonyl)-5,6,8a,9,10,11,12,12a,13,13a-decahydroisoquino[2,1-g][1,6]naphthyridin-8-one;

(8aS,12aS,13aS)-1,2-methylenedioxy-(1-R-phenethylaminocarbonyl)-5,6,8a,9,10,11,12,12a,13,13a-decahydroisoquino[2,1-g][1,6]naphthyridin-8-one; and (8aR,12aR,13aR)-1,2-methylenedioxy-(1-R-phenethylaminocarbonyl)-5,6,8a,9,10,11,12,12a,13,13a-decahydroisoquino[2,1-g][1,6]naphthyridin-8-one;

(8aS,12aS,13aS)-2-chloro-(1-R-phenethylaminocarbonyl)-5,6,8a,9,10,11,12,12a,13,13a-decahydroisoquino[2,1-g][1,6]naphthyridin-8-one; and (8aR,12aR,13aR)-2-chloro-(1-R-phenethylaminocarbonyl)-5,6,8a,9,10,11,12,12a,13,13a-decahydroisoquino[2,1-g][1,6]naphthyridin-8-one;

(8aS,12aS,13aS)-3-chloro-(1-R-phenethylaminocarbonyl)-5,6,8a,9,10,11,12,12a,13,13a-decahydroisoquino[2,1-g][1,6]naphthyridin-8-one; and (8aR,12aR,13aR)-3-chloro-(1-R-phenethylaminocarbonyl)-5,6,8a,9,10,11,12,12a,13,13a-decahydroisoquino[2,1-g][1,6]naphthyridin-8-one;

(8aS,12aS,13aS)-4-chloro-(1-R-phenethylaminocarbonyl)-5,6,8a,9,10,11,12,12a,13,13a-decahydroisoquino[2,1-g][1,6]naphthyridin-8-one; and (8aR,12aR,13aR)-4-chloro-(1-R-phenethylaminocarbonyl)-5,6,8a,9,10,11,12,12a,13,13a-decahydroisoquino[2,1-g][1,6]naphthyridin-8-one;

(8aS,12aS,13aS)-3-bromo-(1-R-phenethylaminocarbonyl)-5,6,8a,9,10,11,12,12a,13,13a-decahydroisoquino[2,1-g][1,6]naphthyridin-8-one; and (8aR,12aR,13aR)-3-bromo-(1-R-phenethylaminocarbonyl)-5,6,8a,9,10,11,12,12a,13,13a-decahydroisoquino[2,1-g][1,6]naphthyridin-8-one;

(8aS,12aS,13aS)-3-fluoro-(1-R-phenethylaminocarbonyl)-5,6,8a,9,10,11,12,12a,13,13a-decahydroisoquino[2,1-g][1,6]naphthyridin-8-one; and (8aR,12aR,13aR)-3-fluoro-(1-R-phenethylaminocarbonyl)-5,6,8a,9,10,11,12,12a,13,13a-decahydroisoquino[2,1-g][1,6]naphthyridin-8-one;

(8aS,12aS,13aS)-2-fluoro-(1-R-phenethylaminocarbonyl)-5,6,8a,9,10,11,12,12a,13,13a-decahydroisoquino[2,1-g][1,6]naphthyridin-8-one; and (8aR,12aR,13aR)-2-fluoro-(1-R-phenethylaminocarbonyl)-5,6,8a,9,10,11,12,12a,13,13a-decahydroisoquino[2,1-g][1,6-]naphthyridin-8-one.

D. Similarly, replacing (±)-3-methoxy-5,6,8aα,9,10,11,12,12aα,13,13aα-decahydroisoquino[2,1-g][1,6]naphthyridin-8-one with the appropriate compound of formula (VI) and following the procedure in paragraph A above, the following compounds of formula (XIII) and (XIV) are prepared:

(8aS,12aS,13aR)-3-methoxy-12-(1-R-phenethylaminocarbonyl)-5,6,8a,9,10,11,12,12a,13,13a-decahydroisoquino[2,1-g][1,6]-naphthyridin-8-one; and (8aR,12aR,13aS)-3-methoxy-12-(1-R-phenethylaminocarbonyl)-5,6,8a,9,10,11,12,12a,13,13a-decahydroisoquino[2,1-g][1,6]naphthyridin-8-one;

(8aS,12aS,13aR)-12-(1-R-phenethylaminocarbonyl)-5,6,8a,9,10,11,12,12a,13,13a-decahydroisoquino[2,1-g][1,6]naphthyridin-8-one; and (8aR,12aR,13aS)-12-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-methylenedioxy-12-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-methylenedioxy-12-(1-R-phenethylaminocarbonyl)-5,6,8a,9,10,11,12,12a,-13,13a-decahydroisoquino[2,1-g][1,6]naphthyridin-8-one;

(8aS,12aS,13aR)-2,3-dimethoxy-12-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-dimethoxy-12-(1-R-phenethylaminocarbonyl)-5,6,8a,9,10,11,12,12a,13,13a-decahydroisoquino[2,1-g][1,6]naphthyridin-8-one;

(8aS,12aS,13aR)-1,4-dimethoxy-12-(1-R-phenethylaminocarbonyl)-5,6,8a,9,10,11,12,12a,13,13a-decahydroisoquino[2,1-g][1,6]naphthyridin-8-one; and (8aR,12aR,13aS)-1,4-dimethoxy-12-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-(ethylene-1,2-dioxy)-12-(1-R-phenethylaminocarbonyl)-5,6,8a,9,10,11,12,12a,13,-13a-decahydroisoquino[2,1-g][1,6]naphthyridin-8-one; and (8aR,12aR,13aS)-2,3-(ethylene-1,2-dioxy)-12-(1-R-phenethylaminocarbonyl)-5,6,8a,9,10,11,12,12a,13,-13a-decahydroisoquino[2,1-g][1,6]-naphthyridin-8-one;

(8aS,12aS,13aR)-1-methyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-1-methyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-2-methyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-2-methyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-methyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-methyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-dimethyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-dimethyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-ethyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-ethyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-isobutyl-(1-R-phenethylaminocarbonyl)-5,6,8a,9,10,11,12,12a,13,-13a-decahydroisoquino[2,1-g][1,6]naphthyridin-8-one; and (8aR,12aR,13aS)-3-isobutyl-(1-R-phenethylaminocarbonyl)-5,6,8a,9,10,11,12,12a,13,-13a-decahydroisoquino[2,1-g][1,6]naphthyridin-8-one;

(8aS,12aS,13aR)-3-n-hexyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-n-hexyl-(1-R-phenethylaminocarbonyl)-5,6,8a,9,10,11,12,12a,13,13a-decahydroisoquino[2,1-g][1,6]naphthyridin-8-one;

(8aS,12aS,13aR)-1-methoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-1-methoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-2-methoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-2-methoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-4-methoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-4-methoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-methoxy-2-methyl-(1-R-phenethylaminocarbonyl)-5,6,8a,9,10,11,12,12a,-13,13a-decahydroisoquino[2,1-g][1,6]naphthyridin-8-one; and (8aR,12aR,13aS)-3-methoxy-2-methyl-(1-R-phenethylaminocarbonyl)-5,6,8a,9,10,11,12,12a,-13,13a-decahydroisoquino[2,1-g][1,6]naphthyridin-8-one;

(8aS,12aS,13aR)-3-ethoxy-(1-R-phenethylaminocarbonyl)-5,6,8a,9,10,11,12,12a,13,13a-decahydroisoquino[2,1-g][1,6]-naphthyridin-8-one; and (8aR,12aR,13aS)-3-ethoxy-(1-R-phenethylaminocarbonyl)-5,6,8a,9,10,11,12,12a,13,13a-decahydroisoquino[2,1-g][1,6]-naphthyridin-8-one;

(8aS,12aS,13aR)-3-isopropoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-isopropoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-isobutoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-isobutoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-n-hexyloxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-n-hexyloxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-hydroxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-hydroxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-dihydroxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-dihydroxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-1,2-dimethoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-1,2-dimethoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-1,4-dimethoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-1,4-dimethoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-3,4-dimethoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-3,4-dimethoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-diethoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-diethoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-2,3-di-n-butoxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-di-n-butoxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-1,2-methylenedioxy-(1-R-phenethylaminocarbonyl)-5,6,8a,9,10,11,12,12a,13,13a-decahydroisoquino[2,1-g][1,6]naphthyridin-8-one; and (8aR,12aR,13aS)-1,2-methylenedioxy-(1-R-phenethylaminocarbonyl)-5,6,8a,9,10,11,12,12a,13,13a-decahydroisoquino[2,1-g][1,6]naphthyridin-8-one;

(8aS,12aS,13aR)-2-chloro-(1-R-phenethylaminocarbonyl)-5,6,8a,9,10,11,12,12a,13,13a-decahydroisoquino[2,1-g][1,6]naphthyridin-8-one; and (8aR,12aR,13aS)-2-chloro-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-chloro-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-chloro-(1-R-phenethylaminocarbonyl)-5,6,8a,9,10,11,12,12a,13,13a-decahydroisoquino[2,1-g][1,6]naphthyridin-8-one;

(8aS,12aS,13aR)-4-chloro-(1-R-phenethylaminocarbonyl)-5,6,8a,9,10,11,12,12a,13,13a-decahydroisoquino[2,1-g][1,6]naphthyridin-8-one; and (8aR,12aR,13aS)-4-chloro-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-bromo-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-bromo-(1-R-phenethylaminocarbonyl)-5,6,8a,9,10,11,12,12a,13,13a-decahydroisoquino[2,1-g][1,6]naphthyridin-8-one;

(8aS,12aS,13aR)-3-fluoro-(1-R-phenethylaminocarbonyl)-5,6,8a,9,10,11,12,12a,13,13a-decahydroisoquino[2,1-g][1,6]naphthyridin-8-one; and (8aR,12aR,13aS)-3-fluoro-(1-R-phenethylaminocarbonyl)-5,6,8a,9,10,11,12,12a,13,13a-decahydroisoquino[2,1-g][1,6]naphthyridin-8-one;

(8aS,12aS,13aR)-2-fluoro-(1-R-phenethylaminocarbonyl)-5,6,8a,9,10,11,12,12a,13,13a-decahydroisoquino[2,1-g][1,6]naphthyridin-8-one; and (8aR,12aR,13aS)-2-fluoro-(1-R-phenethylaminocarbonyl)-5,6,8a,9,10,11,12,12a,13,13a-decahydroisoquino[2,1-g][1,6]naphthyridin-8-one.

PREPARATION 4

Preparation of
(8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine and (8aS,12aR,13aR)-3-methoxy-12-(1-R-phenethylaminocarbonyl)-5,6,8a,9,10,11,12,12a,13,13a-decahydroiso-8H-quino[2,1-g][1,6]naphthyridine and Related Compounds of Formula (IX), (X) and (XV)

A. A solution of 11.5 g of (8aS,12aS,13aS)-3-methoxy-12-(1-R-phenethylaminocarbonyl)-5,6,8a,9,10,11,12,12a,13,13a-decahydroisoquino[2,1-g][1,6]naphthyridin-8-one, in 50 ml of tetrahydrofuran was added slowly to a solution of 2.0 g of lithium aluminum hydride in 75 ml of tetrahydrofuran. The resulting mixture was stirred at reflux for 2 hours, cooled, and treated sequentially with 2.5 ml of water, 2.5 ml of 15% sodium hydroxide, and 7.5 ml of water. The mixture was filtered and the filtrate was evaporated to afford 8.8 g of (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine, a compound of formula (IX), as a foam. The foam was used as such in the next reaction with no further purification.

B. Similarly, replacing (8aS,12aS,13aS)-3-methoxy-12-(1-R-phenethylaminocarbonyl)-5,6,8a,9,10,11,12,-12a,13,13a-decahydroisoquino[2,1-g][1,6]naphthyridin-8-one with other compounds of formula (VII) or (VIII) and following the procedure in paragraph A above, the following compounds of formula (IX) and (X) were prepared:

(8aS,12aR,13aR)-3-methoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aS)-12-(1-R-phenethylaminocarbonyl)-5,6,8a,9,10,11,12,12a,13,13a-decahydro-8H-isoquino[2,1-g][1,6]naphthyridine;

(8aS,12aR,13aR)-12-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-methylenedioxy-12-(1-R-phenethylaminocarbonyl)-5,6,8a,9,10,11,12,1212a,13,13a-decahydro-8H-isoquino[2,1-g][1,6]naphthyridine; and (8aS,12aR,13aR)-2,3-methylenedioxy-12-(1-R-phenethylaminocarbonyl)-5,6,8a,9,10,11,12,12a,13,13a-decahydro-8H-isoquino[2,1-g][1,6]naphthyridine.

C. Similarly, replacing (8aS,12aS,13aS)-3-methoxy-12-(1-R-phenethylaminocarbonyl)-5,6,8a,9,10,11,12,-12a,13,13a-decahydroisoquino[2,1-g][1,6]naphthyridin-8-one with other compounds of formula (VII) or (VIII) and following the procedure in paragraph A above, the following exemplary compounds of formula (IX) and (X) are prepared:

(8aR,12aS,13aS)-2,3-dimethoxy-12-(1-R-phenethylaminocarbonyl)-5,6,8a,9,10,11,12,12a,13,13a-decahydro-8H-isoquino[2,1-g][1,6]naphthyridine;

(8aS,12aR,13aR)-2,3-dimethoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aS)-1,4-dimethoxy-12-(1-R-phenethylaminocarbonyl)-5,6,8a,9,10,11,12,12a,13,13a-decahydro-8H-isoquino[2,1-g][1,6]naphthyridine;

(8aS,12aR,13aR)-1,4-dimethoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-(ethylene-1,2-dioxy)-12-(1-R-phenethylaminocarbonyl)-5,6,8a,9,10,11,12,12a,13,-13a-decahydro-8H-isoquino[2,1-g][1,6]naphthyridine;

(8aS,12aR,13aR)-2,3-(ethylene-1,2-dioxy)-12-(1-R-phenethylaminocarbonyl)-5,6,8a,9,10,11,12,12a,13,-13a-decahydro-8H-isoquino[2,1-g][1,6]naphthyridine;

(8aR,12aS,13aS)-1-methyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-1-methyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-2-methyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-2-methyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-methyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-methyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-dimethyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-2,3-dimethyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-ethyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-ethyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-isobutyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-isobutyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-n-hexyl-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-n-hexyl-(1-R-phenethylaminocarbonyl)-5,6,8a,9,10,11,12,12a,13,13a-decahydro-8H-isoquino[2,1-g][1,6]naphthyridine;

(8aR,12aS,13aS)-1-methoxy-(1-R-phenthylaminocarbonyl)-5,6,8a,9,10,11,12,12a,13,13a-decahydro-8H-isoquino[2,1-g][1,6]naphthyridine;

(8aS,12aR,13aR)-1-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-2-methoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-2-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-4-methoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-4-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-methoxy-2-methyl-(1-R-phenethylaminocarbonyl)-5,6,8a,9,10,11,12,12a,-13,13a-decahydro-8H-isoquino[2,1-g][1,6]naphthyridine;

(8aS,12aR,13aR)-3-methoxy-2-methyl-(1-R-phenethylaminocarbonyl)-5,6,8a,9,10,11,12,12a,-13,13a-decahydro-8H-isoquino[2,1-g][1,6]naphthyridine;

(8aR,12aS,13aS)-3-ethoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-ethoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-isopropoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-isopropoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-isobutoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-isobutoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-n-hexyloxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-n-hexyloxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-hydroxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-hydroxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-dihydroxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-2,3-dihydroxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-1,2-dimethoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-1,2-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-1,4-dimethoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-1,4-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-3,4-dimethoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-3,4-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-diethoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-2,3-diethoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-2,3-di-n-butoxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-2,3-di-n-butoxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-1,2-methylenedioxy-(1-R-phenethylaminocarbonyl)-5,6,8a,9,10,11,12,12a,13,13a-decahydro-8H-isoquino[2,1-g][1,6]naphthyridine;

(8aS,12aR,13aR)-1,2-methylenedioxy-(1-R-phenethylaminocarbonyl)-5,6,8a,9,10,11,12,12a,13,13a-decahydro-8H-isoquino[2,1-g][1,6]naphthyridine;

(8aR,12aS,13aS)-2-chloro-(1-R-phenethylaminocarbonyl)-5,6,8a,9,10,11,12,12a,13,13a-decahydro-8H-isoquino[2,1-g][1,6]naphthyridine;

(8aS,12aR,13aR)-2-chloro-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-chloro-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-chloro-(1-R-phenethylaminocarbonyl)-5,6,8a,9,10,11,12,12a,13,13a-decahydro-8H-isoquino[2,1-g][1,6]naphthyridine;

(8aR,12aS,13aS)-4-chloro-(1-R-phenethylaminocarbonyl)-5,6,8a,9,10,11,12,12a,13,13a-decahydro-8H-isoquino[2,1-g][1,6]naphthyridine;

(8aS,12aR,13aR)-4-chloro-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-bromo-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-bromo-(1-R-phenethylaminocarbonyl)-5,6,8a,9,10,11,12,12a,13,13a-decahydro-8H-isoquino[2,1-g][1,6]naphthyridine;

(8aR,12aS,13aS)-3-fluoro-(1-R-phenethylaminocarbonyl)-5,6,8a,9,10,11,12,12a,13,13a-decahydro-8H-isoquino[2,1-g][1,6]naphthyridine;

(8aS,12aR,13aR)-3-fluoro-(1-R-phenethylaminocarbonyl)-5,6,8a,9,10,11,12,12a,13,13a-decahydro-8H-isoquino[2,1-g][1,6]naphthyridine;

(8aR,12aS,13aS)-2-fluoro-(1-R-phenethylaminocarbonyl)-5,6,8a,9,10,11,12,12a,13,13a-decahydro-8H-isoquino[2,1-g][1,6]naphthyridine; and (8aS,12aR,13aR)-2-fluoro-(1-R-phenethylaminocarbonyl)-5,6,8a,9,10,11,12,12a,13,13a-decahydro-8H-isoquino[2,1-g][1,6]naphthyridine.

D. Similarly, replacing (8aS,12aS,13aS)-3-methoxy-12-(1-R-phenethylaminocarbonyl)-5,6,8a,9,10,11,12,-12a,13,13a-decahydroisoquino[2,1-g][1,6]naphthyridin-8-one with other compounds of formula (XIII) and following the procedure in paragraph A above, the following exemplary compounds of formula (XV) are prepared:

(8aR,12aS,13aR)-3-methoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-methylenedioxy-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-dimethoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-1,4-dimethoxy-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-(ethylene-1,2-dioxy)-12-(1-R-phenethylaminocarbonyl)-5,6,8a,9,10,11,12,12a,13,13a-decahydro-8H-isoquino[2,1-g][1,6]naphthyridine;

(8aR,12aS,13aR)-1-methyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-2-methyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-methyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-dimethyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-ethyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-isobutyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-n-hexyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-1-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-2-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-4-methoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-methoxy-2-methyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-ethoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-isopropoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-isobutoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-n-hexyloxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-hydroxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-dihydroxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-1,2-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-1,4-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-3,4-dimethoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-diethoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-2,3-di-n-butoxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-1,2-methylenedioxy-(1-R-phenethylaminocarbonyl)-5,6,8a,9,10,11,12,12a,13,13a-decahydro-8H-isoquino[2,1-g][1,6]naphthyridine;

(8aR,12aS,13aR)-2-chloro-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-chloro-(1-R-phenethylaminocarbonyl)-5,6,8a,9,10,11,12,12a,13,13a-decahydro-8H-isoquino[2,1-g][1,6]naphthyridine;

(8aR,12aS,13aR)-4-chloro-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-bromo-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-fluoro-(1-R-phenethylaminocarbonyl)-5,6,8a,9,10,11,12,12a,13,13a-decahydro-8H-isoquino[2,1-g][1,6]naphthyridine; and (8aR,12aS,13aR)-2-fluoro-(1-R-phenethylaminocarbonyl)-5,6,8a,9,10,11,12,12a,13,13a-decahydro-8H-isoquino[2,1-g][1,6]naphthyridine.

PREPARATION 5

Preparation of (8aR,12aS,13aS)-3-methoxy-5,6,8a,9,10,11,12,12a,13,13a-decahydro-8H-isoquino[2,1g][1,6]-naphthyridine and (8aS,12aR,13aR)-3-methoxy-5,6,8a,9,10,-11,12,12a,13,13a-decahydro-8H-isoquino[2,1g][1,6]-naphthyridine and Related Compounds of Formula (XI), (XII) and (XVI)

A. A solution of 10.5 g of (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine in 125 ml of 2N sodium n-butoxide in n-butanol was refluxed for 4 hours. After cooling, water was added and the solution acidified with 2N hydrochloric acid. The solution was then extracted with ethyl acetate, the aqueous portion basified with aqueous ammonium hydroxide and extracted further with methylene chloride. Solvent was then removed from the extract under reduced pressure and the residue chromatographed on silica gel, eluting with 10–20% methanol in methylene chloride, to give (8aR,12aS,13aS)-3-methoxy-5,6,8a,9,10,11,12,12a,13,13a-decahydro-8H-isoquino[2,1-g][1,6]naphthyridine, a compound of formula (XI),
mp 125°–127° C., $[\alpha]_D^{25} = -150.7$ (CHCl$_3$)

B. Similarly, replacing (8aR,12aS,13aS)-3-methoxy-12-(1-R-phenethylaminocarbonyl)-5,6,8a,9,10,11,12,-12a,13,13a-decahydro-8H-isoquino[2,1-g][1,6]naphthyridine with other compounds of formula (X) or (XI)

and following the procedure in paragraph A above, the following compounds of formula (XI) and (XII) were prepared:

(8aS,12aR,13aR)-3-methoxy-5,6,8a,9,10,11,12,12a,13,-13a-decahydro-8H-isoquino[2,1-g][1,6naphthyridine, mp 125°–127° C., [α]$_D^{25}$= +154.5 (CHCl$_3$).

(8aR,12aS,13aS)-5,6,8a,9,10,11,12,12a,13,13a-decahydro-8H-isoquino[2,1-g][1,6]naphthyridine;

(8aS,12aR,13aR)-5,6,8a,9,10,11,12,12a,13,13a-decahydro-8H-isoquino[2,1-g][1,6]naphthyridine;

(8aR,12aS,13aS)-2,3-methylenedioxy-5,6,8a,9,10,11,-12,12a,13,13a-decahydro-8H-isoquino[2,1-g][1,6]naphthyridine; and (8aS,12aR,13aR)-2,3-methylenedioxy-5,6,8a,9,10,11,-12,12a,13,13a-decahydro-8H-isoquino[2,1-g][1,6]naphthyridine.

C. Similarly, replacing (8aR,12aS,13aS)-3-methoxy-12-(1-R-phenethylaminocarbonyl)-5,6,8a,9,10,11,12,-12a,13,13a-decahydro-8H-isoquino[2,1-g][1,6]naphthyridine with other compounds of formula (IX) or (X) and following the procedure in paragraph A above, the following exemplary compounds of formula (XI) and (XII) are prepared:

(8aR,12aS,13aS)-2,3-dimethoxy-5,6,8a,9,10,11,12,-12a,13,13a-decahydro-8H-isoquino[2,1-g][1,6]naphthyridine;

(8aS,12aR,13aR)-2,3-dimethoxy-5,6,8a,9,10,11,12,-12a,13,13a-decahydro-8H-isoquino[2,1-g][1,6]naphthyridine;

(8aR,12aS,13aS)-1,4-dimethoxy-5,6,8a,9,10,11,12,-12a,13,13a-decahydro-8H-isoquino[2,1-g][1,6]naphthyridine;

(8aS,12aR,13aR)-1,4-dimethoxy-5,6,8a,9,10,11,12,-12a,13,13a-decahydro-8H-isoquino[2,1-g][1,6]naphthyridine;

(8aR,12aS,13aS)-2,3-(ethylene-1,2-dioxy)-5,6,8a,9,10,11,12,12a,13,13a-decahydro-8H-isoquino[2,1-g][1,6]naphthyridine;

(8aS,12aR,13aR)-2,3-(ethylene-1,2-dioxy)-5,6,8a,9,-10,11,12,12a,13,13a-decahydro-8H-isoquino[2,1-g][1,6]naphthyridine;

(8aR,12aS,13aS)-1-methyl-5,6,8a,9,10,11,12,12a,13,13a-decahydro-8H-isoquino[2,1-g][1,6]naphthyridine;

(8aS,12aR,13aR)-1-methyl-5,6,8a,9,10,11,12,12a,13,13a-decahydro-8H-isoquino[2,1-g][1,6]naphthyridine;

(8aR,12aS,13aS)-2-methyl-5,6,8a,9,10,11,12,12a,13,13a-decahydro-8H-isoquino[2,1-g][1,6]naphthyridine;

(8aS,12aR,13aR)-2-methyl-5,6,8a,9,10,11,12,12a,13,13a-decahydro-8H-isoquino[2,1-g][1,6]naphthyridine;

(8aR,12aS,13aS)-3-methyl-5,6,8a,9,10,11,12,12a,13,13a-decahydro-8H-isoquino[2,1-g][1,6]naphthyridine;

(8aS,12aR,13aR)-3-methyl-5,6,8a,9,10,11,12,12a,13,13a-decahydro-8H-isoquino[2,1-g][1,6]naphthyridine;

(8aR,12aS,13aS)-2,3-dimethyl-5,6,8a,9,10,11,12,12a,-13,13a-decahydro-8H-isoquino[2,1-g][1,6]naphthyridine;

(8aS,12aR,13aR)-2,3-dimethyl-5,6,8a,9,10,11,12,12a,13,-13a-decahydro-8H-isoquino[2,1-g][1,6]naphthyridine;

(8aR,12aS,13aS)-3-ethyl-5,6,8a,9,10,11,12,12a,13,13a-decahydro-8H-isoquino[2,1-g][1,6]naphthyridine;

(8aS,12aR,13aR)-3-ethyl-5,6,8a,9,10,11,12,12a,13,13a-decahydro-8H-isoquino[2,1-g][1,6]naphthyridine;

(8aR,12aS,13aS)-3-isobutyl-5,6,8a,9,10,11,12,12a,13,-13a-decahydro-8H-isoquino[2,1-g][1,6]naphthyridine;

(8aS,12aR,13aR)-3-isobutyl-5,6,8a,9,10,11,12,12a,13,-13a-decahydro-8H-isoquino[2,1-g][1,6]naphthyridine;

(8aR,12aS,13aS)-3-n-hexyl-5,6,8a,9,10,11,12,12a,13,13a-decahydro-8H-isoquino[2,1-g][1,6]naphthyridine;

(8aS,12aR,13aR)-3-n-hexyl-5,6,8a,9,10,11,12,12a,13,13a-decahydro-8H-isoquino[2,1-g][1,6]naphthyridine;

(8aR,12aS,13aS)-1-methoxy-5,6,8a,9,10,11,12,12a,13,-13a-decahydro-8H-isoquino[2,1-g][1,6]naphthyridine;

(8aS,12aR,13aR)-1-methoxy-5,6,8a,9,10,11,12,12a,13,-13a-decahydro-8H-isoquino[2,1-g][1,6]naphthyridine;

(8aR,12aS,13aS)-2-methoxy-5,6,8a,9,10,11,12,12a,13,-13a-decahydro-8H-isoquino[2,1-g][1,6]naphthyridine;

(8aS,12aR,13aR)-2-methoxy-5,6,8a,9,10,11,12,12a,13,-13a-decahydro-8H-isoquino[2,1-g][1,6]naphthyridine;

(8aR,12aS,13aS)-4-methoxy-5,6,8a,9,10,11,12,12a,13,-13a-decahydro-8H-isoquino[2,1-g][1,6]naphthyridine;

(8aS,12aR,13aR)-4-methoxy-5,6,8a,9,10,11,12,12a,13,-13a-decahydro-8H-isoquino[2,1-g][1,6]naphthyridine;

(8aR,12aS,13aS)-3-methoxy-2-methyl-5,6,8a,9,10,11,12,12a,13,13a-decahydro-8H-isoquino[2,1-g][1,6]naphthyridine;

(8aS,12aR,13aR)-3-methoxy-2-methyl-5,6,8a,9,10,11,12,12a,13,13a-decahydro-8H-isoquino[2,1-g][1,6]naphthyridine;

(8aR,12aS,13aS)-3-ethoxy-5,6,8a,9,10,11,12,12a,13,13a-decahydro-8H-isoquino[2,1-g][1,6]naphthyridine;

(8aS,12aR,13aR)-3-ethoxy-5,6,8a,9,10,11,12,12a,13,13a-decahydro-8H-isoquino[2,1-g][1,6]naphthyridine;

(8aR,12aS,13aS)-3-isopropoxy-5,6,8a,9,10,11,12,12a,13,-13a-decahydro-8H-isoquino[2,1-g][1,6]naphthyridine;

(8aS,12aR,13aR)-3-isobutoxy-5,6,8a,9,10,11,12,12a,13,-13a-decahydro-8H-isoquino[2,1-g][1,6]naphthyridine;

(8aR,12aS,13aS)-3-isopropoxy-5,6,8a,9,10,11,12,12a,13,-13a-decahydro-8H-isoquino[2,1-g][1,6]naphthyridine;

(8aS,12aR,13aR)-3-isobutoxy-5,6,8a,9,10,11,12,12a,13,-13a-decahydro-8H-isoquino[2,1-g][1,6]naphthyridine;

(8aR,12aS,13aS)-3-n-hexyloxy-5,6,8a,9,10,11,12,12a,-13,13a-decahydro-8H-isoquino[2,1-g][1,6]naphthyridine;

(8aS,12aR,13aR)-3-n-hexyloxy-5,6,8a,9,10,11,12,-12a,13,13a-decahydro-8H-isoquino[2,1-g][1,6]naphthyridine;

(8aR,12aS,13aS)-3-hydroxy-5,6,8a,9,10,11,12,12a,13,-13a-decahydro-8H-isoquino[2,1-g][1,6]naphthyridine;

(8aS,12aR,13aR)-3-hydroxy-5,6,8a,9,10,11,12,12a,13,-13a-decahydro-8H-isoquino[2,1-g][1,6]naphthyridine;

(8aR,12aS,13aS)-2,3-dihydroxy-5,6,8a,9,10,11,12,-12a,13,13a-decahydro-8H-isoquino[2,1-g][1,6]naphthyridine;

(8aS,12aR,13aR)-2,3-dihydroxy-5,6,8a,9,10,11,12,-12a,13,13a-decahydro-8H-isoquino[2,1-g][1,6]naphthyridine;

(8aR,12aS,13aS)-1,2-dimethoxy-5,6,8a,9,10,11,12,-12a,13,13a-decahydro-8H-isoquino[2,1-g][1,6]naphthyridine;

(8aS,12aR,13aR)-1,2-dimethoxy-5,6,8a,9,10,11,12,-12a,13,13a-decahydro-8H-isoquino[2,1-g][1,6]naphthyridine;

(8aR,12aS,13aS)-1,4-dimethoxy-5,6,8a,9,10,11,12,-12a,13,13a-decahydro-8H-isoquino[2,1-g][1,6]naphthyridine;

(8aS,12aR,13aR)-1,4-dimethoxy-5,6,8a,9,10,11,12,-12a,13,13a-decahydro-8H-isoquino[2,1-g][1,6]naphthyridine;

(8aR,12aS,13aS)-3,4-dimethoxy-5,6,8a,9,10,11,12,-12a,13,13a-decahydro-8H-isoquino[2,1-g][1,6]naphthyridine;

(8aS,12aR,13aR)-3,4-dimethoxy-5,6,8a,9,10,11,12,-12a,13,13a-decahydro-8H-isoquino[2,1-g][1,6]naphthyridine;

(8aR,12aS,13aS)-2,3-diethoxy-5,6,8a,9,10,11,12,12a,13,-13a-decahydro-8H-isoquino[2,1-g][1,6]naphthyridine;

(8aS,12aR,13aR)-2,3-diethoxy-5,6,8a,9,10,11,12,12a,13,-13a-decahydro-8H-isoquino[2,1-g][1,6]naphthyridine;

(8aR,12aS,13aS)-2,3-di-n-butoxy-5,6,8a,9,10,11,12,-12a,13,13a-decahydro-8H-isoquino[2,1-g][1,6]naphthyridine;

(8aS,12aR,13aR)-2,3-di-n-butoxy-5,6,8a,9,10,11,12,-12a,13,13a-decahydro-8H-isoquino[2,1-g][1,6]naphthyridine;

(8aR,12aS,13aS)-1,2-methylenedioxy-5,6,8a,9,10,11,12,-12a,13,13a-decahydro-8H-isoquino[2,1-g][1,6]naphthyridine;

(8aS,12aR,13aR)-1,2-methylenedioxy-5,6,8a,9,10,11,12,-12a,13,13a-decahydro-8H-isoquino[2,1-g][1,6]naphthyridine;

(8aR,12aS,13aS)-2-chloro-5,6,8a,9,10,11,12,12a,13,13a-decahydro-8H-isoquino[2,1-g][1,6]naphthyridine;

(8aS,12aR,13aR)-2-chloro-5,6,8a,9,10,11,12,12a,13,13a-decahydro-8H-isoquino[2,1-g][1,6]naphthyridine;

(8aR,12aS,13aS)-3-chloro-5,6,8a,9,10,11,12,12a,13,13a-decahydro-8H-isoquino[2,1-g][1,6]naphthyridine;

(8aS,12aR,13aR)-3-chloro-5,6,8a,9,10,11,12,12a,13,13a-decahydro-8H-isoquino[2,1-g][1,6]naphthyridine;

(8aR,12aS,13aS)-4-chloro-5,6,8a,9,10,11,12,12a,13,13a-decahydro-8H-isoquino[2,1-g][1,6]naphthyridine;

(8aS,12aR,13aR)-4-chloro-5,6,8a,9,10,11,12,12a,13,13a-decahydro-8H-isoquino[2,1-g][1,6]naphthyridine;

(8aR,12aS,13aS)-3-bromo-5,6,8a,9,10,11,12,12a,13,13a-decahydro-8H-isoquino[2,1-g][1,6]naphthyridine;

(8aS,12aR,13aR)-3-bromo-5,6,8a,9,10,11,12,12a,13,13a-decahydro-8H-isoquino[2,1-g][1,6]naphthyridine;

(8aR,12aS,13aS)-3-fluoro-5,6,8a,9,10,11,12,12a,13,13a-decahydro-8H-isoquino[2,1-g][1,6]naphthyridine;

(8aS,12aR,13aR)-3-fluoro-5,6,8a,9,10,11,12,12a,13,13a-decahydro-8H-isoquino[2,1-g][1,6]naphthyridine;

(8aR,12aS,13aS)-2-fluoro-5,6,8a,9,10,11,12,12a,13,13a-decahydro-8H-isoquino[2,1-g][1,6]naphthyridine;

(8aS,12aR,13aR)-2-fluoro-5,6,8a,9,10,11,12,12a,13,13a-decahydro-8H-isoquino[2,1-g][1,6]naphthyridine.

D. Similarly, replacing (8aR,12aS,13aS)-3-methoxy-12-(1-R-phenethylaminocarbonyl)-5,6,8a,9,10,11,12,-12a,13,13a-decahydro-8H-isoquino[2,1-g][1,6]naphthyridine with other compounds of formula (XV) and following the procedure in paragraph A above, the following exemplary compounds of formula (XVI) were prepared:

(8aR,12aS,13aS)-3-methoxy-5,6,8a,9,10,11,12,12a,13,-13a-decahydro-8H-isoquino[2,1-g][1,6]naphthyridine; mp 110°-112° C., $[\alpha]_D^{25} = +101.5$ (CHCl$_3$)

(8aR,12aS,13aR)-2,3-methylenedioxy-5,6,8a,9,10,11,12,-12a,13,13a-decahydro-8H-isoquino[2,1-g][1,6]naphthyridine, E. Similarly, replacing (8aR,12aS,13aS)-3-methoxy12-(1-R-phenethylaminocarbonyl)-5,6,8a,9,10,11,12,-12a,13,13a-decahydro-8H-isoquino[2,1-g][1,6]naphthyridine with other compounds of formula (XV) and following the procedure in paragraph A above, the following exemplary compounds of formula (XVI) are prepared:

(8aR,12aS,13aR)-5,6,8a,9,10,11,12,12a,13,13a-decahydro-8H-isoquino[2,1-g][1,6]naphthyridine;

(8aR,12aS,13aR)-2,3-dimethoxy-5,6,8a,9,10,11,12,-12a,13,13a-decahydro-8H-isoquino[2,1-g][1,6]naphthyridine;

(8aR,12aS,13aR)-1,4-dimethoxy-5,6,8a,9,10,11,12,-12a,13,13a-decahydro-8H-isoquino[2,1-g][1,6]naphthyridine;

(8aR,12aS,13aR)-2,3-(ethylene-1,2-dioxy)-5,6,8a,9,-10,11,12,12a,13,13a-decahydro-8H-isoquino[2,1-g][1,6]naphthyridine;

(8aR,12aS,13aR)-1-methyl-5,6,8a,9,10,11,12,12a,13,13a-decahydro-8H-isoquino[2,1-g][1,6]naphthyridine;

(8aR,12aS,13aR)-2-methyl-5,6,8a,9,10,11,12,12a,13,13a-decahydro-8H-isoquino[2,1-g][1,6]naphthyridine;

(8aR,12aS,13aR)-3-methyl-5,6,8a,9,10,11,12,12a,13,13a-decahydro-8H-isoquino[2,1-g][1,6]naphthyridine;

(8aR,12aS,13aR)-2,3-dimethyl-5,6,8a,9,10,11,12,12a,13,-13a-decahydro-8H-isoquino[2,1-g][1,6]naphthyridine;

(8aR,12aS,13aR)-3-ethyl-5,6,8a,9,10,11,12,12a,13,13a-decahydro-8H-isoquino[2,1-g][1,6]naphthyridine;

(8aR,12aS,13aR)-3-isobutyl-5,6,8a,9,10,11,12,12a,13,-13a-decahydro-8H-isoquino[2,1-g][1,6]naphthyridine;

(8aR,12aS,13aR)-3-n-hexyl-5,6,8a,9,10,11,12,12a,13,13a-decahydro-8H-isoquino[2,1-g][1,6]naphthyridine;

(8aR,12aS,13aR)-1-methoxy-5,6,8a,9,10,11,12,12a,13,-13a-decahydro-8H-isoquino[2,1-g][1,6]naphthyridine;

(8aR,12aS,13aR)-2-methoxy-5,6,8a,9,10,11,12,12a,13,-13a-decahydro-8H-isoquino[2,1-g][1,6]naphthyridine;

(8aR,12aS,13aR)-4-methoxy-5,6,8a,9,10,11,12,12a,13,-13a-decahydro-8H-isoquino[2,1-g][1,6]naphthyridine;

(8aR,12aS,13aR)-3-methoxy-2-methyl-5,6,8a,9,10,11,12,12a,13,13a-decahydro-8H-isoquino[2,1-g][1,6]naphthyridine;

(8aR,12aS,13aR)-3-ethoxy-5,6,8a,9,10,11,12,12a,13,13a-decahydro-8H-isoquino[2,1-g][1,6]naphthyridine;

(8aR,12aS,13aR)-3-isopropoxy-5,6,8a,9,10,11,12,-12a,13,13a-decahydro-8H-isoquino[2,1-g][1,6]naphthyridine;

(8aR,12aS,13aR)-3-isopropoxy-5,6,8a,9,10,11,12,-12a,13,13a-decahydro-8H-isoquino[2,1-g][1,6]naphthyridine;

(8aR,12aS,13aR)-3-n-hexyloxy-5,6,8a,9,10,11,12,-12a,13,13a-decahydro-8H-isoquino[2,1-g][1,6]naphthyridine;

(8aR,12aS,13aR)-3-hydroxy-5,6,8a,9,10,11,12,12a,13,-13a-decahydro-8H-isoquino[2,1-g][1,6]naphthyridine;

(8aR,12aS,13aR)-2,3-dihydroxy-5,6,8a,9,10,11,12,-12a,13,13a-decahydro-8H-isoquino[2,1-g][1,6]naphthyridine;

(8aR,12aS,13aR)-1,2-dimethoxy-5,6,8a,9,10,11,12,-12a,13,13a-decahydro-8H-isoquino[2,1-g][1,6]naphthyridine;

(8aR,12aS,13aR)-1,4-dimethoxy-5,6,8a,9,10,11,12,-12a,13,13a-decahydro-8H-isoquino[2,1-g][1,6]naphthyridine;

(8aR,12aS,13aR)-3,4-dimethoxy-5,6,8a,9,10,11,12,-12a,13,13a-decahydro-8H-isoquino[2,1-g][1,6]naphthyridine;

(8aR,12aS,13aR)-2,3-diethoxy-5,6,8a,9,10,11,12,12a,13,-13a-decahydro-8H-isoquino[2,1-g][1,6]naphthyridine;

(8aR,12aS,13aR)-2,3-di-n-butoxy-5,6,8a,9,10,11,12,-12a,13,13a-decahydro-8H-isoquino[2,1-g][1,6]naphthyridine;

(8aR,12aS,13aR)-1,2-methylenedioxy-5,6,8a,9,10,11,12,-12a,13,13a-decahydro-8H-isoquino[2,1-g][1,6]naphthyridine;

(8aR,12aS,13aR)-2-chloro-5,6,8a,9,10,11,12,12a,13,13a-decahydro-8H-isoquino[2,1-g][1,6]naphthyridine;

(8aR,12aS,13aR)-3-chloro-5,6,8a,9,10,11,12,12a,13,13a-decahydro-8H-isoquino[2,1-g][1,6]naphthyridine;

(8aR,12aS,13aR)-4-chloro-5,6,8a,9,10,11,12,12a,13,13a-decahydro-8H-isoquino[2,1-g][1,6]naphthyridine;

(8aR,12aS,13aR)-3-bromo-5,6,8a,9,10,11,12,12a,13,13a-decahydro-8H-isoquino[2,1-g][1,6]naphthyridine;

(8aR,12aS,13aR)-3-fluoro-5,6,8a,9,10,11,12,12a,13,13a-decahydro-8H-isoquino[2,1-g][1,6]naphthyridine; and (8aR,12aS,13aR)-2-fluoro-5,6,8a,9,10,11,12,12a,13,13a-decahydro-8H-isoquino[2,1-g][1,6]naphthyridine.

EXAMPLE 1

Preparation of (8aR,12aS,13aS)-3-methoxy-12-methanesulfonyl-5,6,8a,9,10,11,12,12a,13,13a-decahydro-8H-isoquino[2,1g][1,6]naphthyridine hydrochloride and Related Compounds of Formula (1) and (2)

A. A solution of 0.4 g of (8aR,12aS,13aS)-3-methoxy-5,6,8a,9,10,11,12,12a,13,13a-decahydro-8H-isoquino[2,1-g][1,6]naphthyridine (XI) in 15 ml of methylene chloride and 0.5 ml of triethylamine was cooled in an ice bath and 0.5 ml of methanesulfonyl chloride was added. The mixture was stirred at room temperature for 1 hour, diluted with 100 ml of ether, and extracted with dilute HCl. The aqueous HCl layer was basified with NH₄OH and extracted with methylene chloride. The methylene chloride was evaporated to a residue, mp 165°-166° C., $[\alpha]_D^{25}=-55.5$ (CHCl₃). The residue was optionally dissolved in ethanol and acidified with ethanolic HCl. Crystallization was induced by adding a small amount of diethylether. Filtration afforded 0.4 g of
(8aR,12aS,13aS)-3-methoxy-12-methanesulfonyl-5,6,8a,9,10,11,12,12a,13,13a-decahydro-8H-isoquino[2,1-g][1,6]naphthyridine hydrochloride, mp 256°-258° C., $[\alpha]_D^{25}=+13.1$ (CHCl₃).

B. Similarly, optionally replacing (8aR,12aS,13aS)-3-methoxy-5,6,8aα9,10,11,12,12a,13,13a-decahydro-8H-isoquino[2,1-g][1,6]naphthyridine with other compounds of formula (XI), optionally replacing methanesulfonyl chloride with other sulfonyl halides of formula ZSO₂R and following the procedure in paragraph A above, the following compounds of formula (1) were prepared:

(8aR,12aS,13aS)-3-methoxy-12-N,N-dimethylaminosulfonyl-5,6,8a,9,10,11,12,12a,13,13a-decahydro-8H-isoquino[2,1-g][1,6]naphthyridine hydrochloride, mp 242°-243° C., $[\alpha]_D^{25}=+8.21$ (CH₃OH).

(8aR,12aS,13aS)-12-methanesulfonyl-5,6,8a,9,10,11,12,-12a,13,13a-decahydro-8H-isoquino[2,1-g][1,6]naphthyridine hydrochloride, mp 266°-267° C., $[\alpha]_D^{25}=+0.1$ (H₂O)

(8aR,12aS,13aS)-2,3-methylenedioxy-12-methanesulfonyl-5,6,8a,9,10,11,12,12a,13,13a-decahydro-8H-isoquino[2,1-g][1,6]naphthyridine hydrochloride, mp 263°-265° C., $[\alpha]_D^{25}=-17.0$(CH₃OH)

C. Similarly, optionally replacing (8aR,12aS,13aS)-3-methoxy-5,6,8aα,9,10,11,12,12a,13,13a-decahydro-8H-isoquino[2,1-g][1,6]naphthyridine with compounds of formula (XVI), optionally replacing methanesulfonyl chloride with other sulfonyl halides of formula ZSO₂R and following the procedure in paragraph A above, the following compounds of formula (2) were prepared:

(8aR,12aS,13aR)-3-methoxy-12-methanesulfonyl-5,6,8a,9,10,11,12,12a,13,13a-decahydro-8H-isoquino[2,1-g][1,6]naphthyridine, mp 140°-143° C., $[\alpha]_D^{25}=+17.6$ (CHCl₃).

(8aR,12aS,13aR)-2,3-methylenedioxy-12-methanesulfonyl-5,6,8a,9,10,11,12,12a,13,13a-decahydro-8H-isoquino[2,1-g][1,6]naphthyridine, mp 219°-220° C., $[\alpha]_D^{25}=+45.3$ (CHCl₃)

D. Similarly, optionally replacing (8aR,12aS,13aS)-3-methoxy-5,6,8aα,9,10,11,12,12a,13,13a-decahydro-8H-isoquino[2,1-g][1,6]naphthyridine with other compounds of formula (XI), optionally replacing methanesulfonyl chloride with other sulfonyl halides of formula ZSO₂R and following the procedure in paragraph A above, the following compounds of formula (1) are prepared:

(8aR,12aS,13aS)-12-ethanesulfonyl-5,6,8a,9,10,11,12,-12a,13,13a-decahydro-8H-isoquino[2,1-g][1,6]naphthyridine hydrochloride;

(8aR,12aS,13aS)-12-(1-propanesulfonyl)-5,6,8a,9,10,11,12,12a,13,13a-decahydro-8H-isoquino[2,1-g][1,6]naphthyridine hydrochloride;

(8aR,12aS,13aS)-12-(1-butanesulfonyl)-5,6,8a,9,10,11,12,12a,13,13a-decahydro-8H-isoquino[2,1-g][1,6]naphthyridine hydrochloride;

(8aR,12aS,13aS)-12-(2-methylpropanesulfonyl)-5,6,8a,9,10,11,12,12a,13,13a-decahydro-8H-isoquino[2,1-g][1,6]naphthyridine hydrochloride;

(8aR,12aS,13aS)-12-phenylsulfonyl-5,6,8a,9,10,11,12,-12a,13,13a-decahydro-8H-isoquino[2,1-g][1,6]naphthyridine hydrochloride;

(8aR,12aS,13aS)-12-(4-methoxyphenylsulfonyl)-5,6,8a,9,10,11,12,12a,13,13a-decahydro-8H-isoquino[2,1-g][1,6]naphthyridine hydrochloride;

(8aR,12aS,13aS)-12-(4-chlorophenylsulfonyl)-5,6,8a,9,10,11,12,12a,13,13a-decahydro-8H-isoquino[2,1-g][1,6]naphthyridine hydrochloride;

(8aR,12aS,13aS)-12-(4-fluorophenylsulfonyl)-5,6,8a,9,10,11,12,12a,13,13a-decahydro-8H-isoquino[2,1-g][1,6]naphthyridine hydrochloride;

(8aR,12aS,13aS)-12-(2-methoxyethanesulfonyl)-5,6,8a,9,10,11,12,12a,13,13a-decahydro-8H-isoquino[2,1-g][1,6]naphthyridine hydrochloride;

(8aR,12aS,13aS)-3-methoxy-12-ethanesulfonyl-5,6,8a,9,10,11,12,12a,13,13a-decahydro-8H-isoquino[2,1-g][1,6]naphthyridine hydrochloride;

(8aR,12aS,13aS)-3-methoxy-12-(1-propanesulfonyl)-5,6,8a,9,10,11,12,12a,13,13a-decahydro-8H-isoquino[2,1-g][1,6]naphthyridine hydrochloride;

(8aR,12aS,13aS)-3-methoxy-12-phenylsulfonyl-
5,6,8a,9,10,11,12,12a,13,13a-decahydro-8H-
isoquino[2,1-g][1,6]naphthyridine hydrochloride;
(8aR,12aS,13aS)-3-methoxy-12-(2-methylpropanesulfonyl)-5,6,8a,9,10,11,12,12a,13,13a-decahydro-8H-
isoquino[2,1-g][1,6]naphthyridine hydrochloride;
(8aR,12aS,13aS)-3-methoxy-12-(1-piperazinosulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-(1-morpholinosulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-(1-piperidinosulfonyl)-
5,6,8a,9,10,11,12,12a,13,13a-decahydro-8H-
isoquino[2,1-g][1,6]naphthyridine hydrochloride;
(8aR,12aS,13aS)-2,3-dimethoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-1,4-dimethoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-2,3-dimethoxy-12-(2-methylpropanesulfonyl)-5,6,8a,9,10,11,12,12a,13,13a-decahydro-8H-isoquino[2,1-g][1,6]naphthyridine hydrochloride;
(8aR,12aS,13aS)-2,3-methylenedioxy-12-methanesulfonyl-5,6,8a,9,10,11,12,12a,13,13a-decahydro-8H-
isoquino[2,1-g][1,6]naphthyridine hydrochloride;
(8aR,12aS,13aS)-2,3-(ethylene-1,2-dioxy)-12-
methanesulfonyl-5,6,8a,9,10,11,12,12a,13,13a-decahydro-8H-isoquino[2,1-g][1,6]naphthyridine hydrochloride;
(8aR,12aS,13aS)-2,3-methylenedioxy-12-(2-methylpropanesulfonyl)-5,6,8a,9,10,11,12,12a,13,13a-decahydro-8H-isoquino[2,1-g][1,6]naphthyridine hydrochloride;
(8aR,12aS,13aS)-3-methoxy-12-(2-methoxyethanesulfonyl)-5,6,8a,9,10,11,12,12a,13,13a-decahydro-8H-
isoquino[2,1-g][1,6]naphthyridine hydrochloride;
(8aR,12aS,13aS)-12-(4-aminophenylsulfonyl)-
5,6,8a,9,10,11,12,12a,13,13a-decahydro-8H-
isoquino[2,1-g][1,6]naphthyridine hydrochloride;
(8aR,12aS,13aS)-12-(2-hydroxyethanesulfonyl)-
5,6,8a,9,10,11,12,12a,13,13a-decahydro-8H-
isoquino[2,1-g][1,6]naphthyridine hydrochloride;
(8aR,12aS,13aS)-1-methyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-2-methyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-methyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-ethyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-2,3-dimethyl-12-methanesulfonyl-
5,6,8a,9,10,11,12,12a,13,13a-decahydro-8H-
isoquino[2,1g][1,6]naphthyridine hydrochloride;
(8aR,12aS,13aS)-3-isobutyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-2-n-hexyl-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-methoxy-2-methyl-12-methanesulfonyl-5,6,8a,9,10,11,12,12a,13,13a-decahydro-8H-
isoquino[2,1-g][1,6]naphthyridine hydrochloride;
(8aR,12aS,13aS)-1-methoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-2-methoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-4-methoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-ethoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-ethoxy-12-ethanesulfonyl-
5,6,8a,9,10,11,12,12a,13,13a-decahydro-8H-
isoquino[2,1-g][1,6]naphthyridine hydrochloride;
(8aR,12aS,13aS)-3-isopropoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-isobutoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-n-hexyloxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-hydroxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-2,3-dihydroxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-1,2-dimethoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-2,3-diethoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-2,3-di-n-butoxy-12-methanesulfonyl-
5,6,8a,9,10,11,12,12a,13,13a-decahydro-8H-
isoquino[2,1-g][1,6]naphthyridine hydrochloride;
(8aR,12aS,13aS)-3,4-methylenedioxy-12-methanesulfonyl-5,6,8a,9,10,11,12,12a,13,13a-decahydro-8H-
isoquino[2,1-g][1,6]naphthyridine hydrochloride;
(8aR,12aS,13aS)-2-chloro-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-chloro-12-methanesulfonyl-
5,6,8a,9,10,11,12,12a,13,13a-decahydro-8H-
isoquino[2,1-g][1,6]naphthyridine hydrochloride;
(8aR,12aS,13aS)-2-fluoro-12-methanesulfonyl-
5,6,8a,9,10,11,12,12a,13,13a-decahydro-8H-
isoquino[2,1-g][1,6]naphthyridine hydrochloride;
(8aR,12aS,13aS)-3-fluoro-12-methanesulfonyl-
5,6,8a,9,10,11,12,12a,13,13a-decahydro-8H-
isoquino[2,1-g][1,6]naphthyridine hydrochloride;
(8aR,12aS,13aS)-12-aminosulfonyl-5,6,8a,9,10,11,12,-
12a,13,13a-decahydro-8H-isoquino[2,1-g][1,6]naphthyridine hydrochloride;
(8aR,12aS,13aS)-3-methoxy-12-aminosulfonyl-
5,6,8a,9,10,11,12,12a,13,13a-decahydro-8H-
isoquino[2,1-g][1,6]naphthyridine hydrochloride;
(8aR,12aS,13aS)-12-methylaminosulfonyl-
5,6,8a,9,10,11,12,12a,13,13a-decahydro-8H-
isoquino[2,1-g][1,6]naphthyridine hydrochloride;

(8aR,12aS,13aS)-12-diethylaminosulfonyl-5,6,8a,9,10,11,12,12a,13,13a-decahydro-8H-isoquino[2,1-g][1,6]naphthyridine hydrochloride;
(8aR,12aS,13aS)-12-di-n-hexylaminosulfonyl-5,6,8a,9,10,11,12,12a,13,13a-decahydro-8H-isoquino[2,1-g][1,6]naphthyridine hydrochloride;
(8aR,12aS,13aS)-12-(1-piperazinosulfonyl)-5,6,8a,9,10,11,12,12a,13,13a-decahydro-8H-isoquino[2,1-g][1,6]naphthyridine hydrochloride;
(8aR,12aS,13aS)-12-(1-morpholinosulfonyl)-5,6,8a,9,10,11,12,12a,13,13a-decahydro-8H-isoquino[2,1-g][1,6]naphthyridine hydrochloride;
(8aR,12aS,13aS)-12-(1-piperidinosulfonyl)-5,6,8a,9,10,11,12,12a,13,13a-decahydro-8H-isoquino[2,1-g][1,6]naphthyridine hydrochloride;
(8aR,12aS,13aS)-3-methyl-12-ethanesulfonyl-5,6,8a,9,10,11,12,12a,13,13a-decahydro-8H-isoquino[2,1-g][1,6]naphthyridine hydrochloride;
(8aR,12aS,13aS)-3-ethoxy-12-ethanesulfonyl-5,6,8a,9,10,11,12,12a,13,13a-decahydro-8H-isoquino[2,1-g][1,6]naphthyridine hydrochloride;
(8aR,12aS,13aS)-3-n-hexyloxy-12-ethanesulfonyl-5,6,8a,9,10,11,12,12a,13,13a-decahydro-8H-isoquino[2,1-g][1,6]naphthyridine hydrochloride;
(8aR,12aS,13aS)-2,3-diethoxy-12-ethanesulfonyl-5,6,8a,9,10,11,12,12a,13,13a-decahydro-8H-isoquino[2,1-g][1,6]naphthyridine hydrochloride;
(8aR,12aS,13aS)-3-methyl-12-(1-n-hexanesulfonyl)-5,6,8a,9,10,11,12,12a,13,13a-decahydro-8H-isoquino[2,1-g][1,6]naphthyridine hydrochloride;
(8aR,12aS,13aS)-3-methoxy-12-(1-n-hexanesulfonyl)-5,6,8a,9,10,11,12,12a,13,13a-decahydro-8H-isoquino[2,1-g][1,6]naphthyridine hydrochloride;
(8aR,12aS,13aS)-2,3-dimethoxy-12-(1-n-hexanesulfonyl)-5,6,8a,9,10,11,12,12a,13,13a-decahydro-8H-isoquino[2,1-g][1,6]naphthyridine hydrochloride;
(8aR,12aS,13aS)-3-methoxy-12-phenylsulfonyl-5,6,8a,9,10,11,12,12a,13,13a-decahydro-8H-isoquino[2,1-g][1,6]naphthyridine hydrochloride;
(8aR,12aS,13aS)-3-methoxy-12-(N,N-dimethylaminosulfonyl)-5,6,8a,9,10,11,12,12a,13,13a-decahydro-8H-isoquino[2,1-g][1,6]naphthyridine hydrochloride;
(8aR,12aS,13aS)-3-methoxy-12-(t-butylaminosulfonyl)-5,6,8a,9,10,11,12,12a,13,13a-decahydro-8H-isoquino[2,1-g][1,6]naphthyridine hydrochloride;
(8aR,12aS,13aS)-2,3-dimethoxy-12-(N,N-dimethylaminosulfonyl)-5,6,8a,9,10,11,12,12a,13,13a-decahydro-8H-isoquino[2,1-g][1,6]naphthyridine hydrochloride;
(8aR,12aS,13aS)-2,3-methylenedioxy-12-(N,N-dimethylaminosulfonyl)-5,6,8a,9,10,11,12,12a,13,13a-decahydro-8H-isoquino[2,1-g][1,6]naphthyridine hydrochloride; and
(8aR,12aS,13aS)-2-methyl-12-(2-methoxymethanesulfonyl)-5,6,8a,9,10,11,12,12a,13,13a-decahydro-8H-isoquino[2,1-g][1,6]naphthyridine hydrochloride.

Similarly, optionally replacing (8aR,12aS,13aS)-3-methoxy-5,6,8aα,9,10,11,12,12a,13,13a-decahydro-8H-isoquino[2,1-g][1,6]naphthyridine with other compounds of formula (XVI), optionally replacing methanesulfonyl chloride with other sulfonyl halides of formula ZSO$_2$R and following the procedure in paragraph A above, the following compounds of formula (2) are prepared:

(8aR,12aS,13aR)-12-ethanesulfonyl-5,6,8a,9,10,11,12,12a,13,13a-decahydro-8H-isoquino[2,1-g][1,6]naphthyridine hydrochloride;
(8aR,12aS,13aR)-12-(1-propanesulfonyl)-5,6,8a,9,10,11,12,12a,13,13a-decahydro-8H-isoquino[2,1-g][1,6]naphthyridine hydrochloride;
(8aR,12aS,13aR)-12-(1-butanesulfonyl)-5,6,8a,9,10,11,12,12a,13,13a-decahydro-8H-isoquino[2,1-g][1,6]naphthyridine hydrochloride;
(8aR,12aS,13aR)-12-(2-methylpropanesulfonyl)-5,6,8a,9,10,11,12,12a,13,13a-decahydro-8H-isoquino[2,1-g][1,6]naphthyridine hydrochloride;
(8aR,12aS,13aR)-12-phenylsulfonyl-5,6,8a,9,10,11,12,12a,13,13a-decahydro-8H-isoquino[2,1-g][1,6]naphthyridine hydrochloride;
(8aR,12aS,13aR)-12-(4-methoxyphenylsulfonyl)-5,6,8a,9,10,11,12,12a,13,13a-decahydro-8H-isoquine[2,1-g][1,6]naphthyridine hydrochloride;
(8aR,12aS,13aR)-12-(4-chlorophenylsulfonyl)-5,6,8a,9,10,11,12,12a,13,13a-decahydro-8H-isoquino[2,1-g][1,6]naphthyridine hydrochloride;
(8aR,12aS,13aR)-12-(4-fluorophenylsulfonyl)-5,6,8a,9,10,11,12,12a,13,13a-decahydro-8H-isoquino[2,1-g][1,6]naphthyridine hydrochloride;
(8aR,12aS,13aR)-12-(2-methoxyethanesulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-ethanesulfonyl-5,6,8a,9,10,11,12,12a,13,13a-decahydro-8H-isoquino[2,1-g][1,6]naphthyridine hydrochloride;
(8aR,12aS,13aR)-3-methoxy-12-(1-propanesulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-phenylsulfonyl-5,6,8a,9,10,11,12,12a,13,13a-decahydro-8H-isoquino[2,1-g][1,6]naphthyridine hydrochloride;
(8aR,12aS,13aR)-3-methoxy-12-(2-methylpropanesulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-(1-piperazinosulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-(1-morpholinosulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-(1-piperidinosulfonyl)-5,6,8a,9,10,11,12,12a,13,13a-decahydro-8H-isoquino[2,1-g][1,6]naphthyridine hydrochloride;
(8aR,12aS,13aR)-2,3-dimethoxy-12-methanesulfonyl-5,6,8a,9,10,11,12,12a,13,13a-decahydro-8H-isoquino[2,1-g][1,6]naphthyridine hydrochloride;
(8aR,12aS,13aR)-1,4-dimethoxy-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-dimethoxy-12-(2-methylpropanesulfonyl)-5,6,8a,9,10,11,12,12a,13,13a-decahydro-8H-isoquino[2,1-g][1,6]naphthyridine hydrochloride;
(8aR,12aS,13aR)-2,3-methylenedioxy-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-(ethylene-1,2-dioxy)-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-methylenedioxy-12-(2-methylpropanesulfonyl)-5,6,8a,9,10,11,12,12a,13,13a-decahydro-8H-isoquino[2,1-g][1,6]naphthyridine hydrochloride;

(8aR,12aS,13aR)-3-methoxy-12-(2-methoxyethanesulfonyl)-5,6,8a,9,10,11,12,12a,13,13a-decahydro-8H-isoquino[2,1-g][1,6]naphthyridine hydrochloride;
(8aR,12aS,13aR)-12-(4-aminophenylsulfonyl)-5,6,8a,9,10,11,12,12a,13,13a-decahydro-8H-isoquino[2,1-g][1,6]naphthyridine hydrochloride;
(8aR,12aS,13aR)-12-(2-hydroxyethanesulfonyl)-5,6,8a,9,10,11,12,12a,13,13a-decahydro-8H-isoquino[2,1-g][1,6]naphthyridine hydrochloride;
(8aR,12aS,13aR)-1-methyl-12-methanesulfonyl-5,6,8a,9,10,11,12,12a,13,13a-decahydro-8H-isoquino[2,1-g][1,6]naphthyridine hydrochloride;
(8aR,12aS,13aR)-2-methyl-12-methanesulfonyl-5,6,8a,9,10,11,12,12a,13,13a-decahydro-8H-isoquino[2,1-g][1,6]naphthyridine hydrochloride;
(8aR,12aS,13aR)-3-methyl-12-methanesulfonyl-5,6,8a,9,10,11,12,12a,13,13a-decahydro-8H-isoquino[2,1-g][1,6]naphthyridine hydrochloride;
(8aR,12aS,13aR)-3-ethyl-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-dimethyl-12-methanesulfonyl-5,6,,-8a,9,10,11,12,12a,13,13a-decahydro-8H-isoquino[2,1-g][1,6]naphthyridine hydrochloride;
(8aR,12aS,13aR)-3-isobutyl-12-methanesulfonyl-5,6,8a,9,10,11,12,12a,13,13a-decahydro-8H-isoquino[2,1-g][1,6]naphthyridine hydrochloride;
(8aR,12aS,13aR)-2-n-hexyl-12-methanesulfonyl-5,6,8a,9,10,11,12,12a,13,13a-decahydro-8H-isoquino[2,1-g][1,6]naphthyridine hydrochloride;
(8aR,12aS,13aR)-3-methoxy-2methyl-12-methanesulfonyl-5,6,8a,9,10,11,12,12a,13,13a-decahydro-8H-isoquino[2,1-g][1,6]naphthyridine hydrochloride;
(8aR,12aS,13aR)-1-methoxy-12-methanesulfonyl-5,6,8a,9,10,11,12,12a,13,13a-decahydro-8H-isoquino[2,1-g][1,6]naphthyridine hydrochloride;
(8aR,12aS,13aR)-2-methoxy-12-methanesulfonyl-5,6,8a,9,10,11,12,12a,13,13a-decahydro-8H-isoquino[2,1-g][1,6]naphthyridine hydrochloride;
(8aR,12aS,13aR)-4-methoxy-12-methanesulfonyl-5,6,8a,9,10,11,12,12a,13,13a-decahydro-8H-isoquino[2,1-g][1,6]naphthyridine hydrochloride;
(8aR,12aS,13aR)-3-ethoxy-12-methanesulfonyl-5,6,8a,9,10,11,12,12a,13,13a-decahydro-8H-isoquino[2,1-g][1,6]naphthyridine hydrochloride;
(8aR,12aS,13aR)-3-ethoxy-12-ethanesulfonyl-5,6,8a,9,10,11,12,12a,13,13a-decahydro-8H-isoquino[2,1-g][1,6]naphthyridine hydrochloride;
(8aR,12aS,13aR)-3-isopropoxy-12-methanesulfonyl-5,6,-8a,9,10,11,12,12a,13,13a-decahydro-8H-isoquino[2,1-g][1,6]naphthyridine hydrochloride;
(8aR,12aS,13aR)-3-isobutoxy-12-methanesulfonyl-5,6,-8a,9,10,11,12,12a,13,13a-decahydro-8H-isoquino[2,1-g][1,6]naphthyridine hydrochloride;
(8aR,12aS,13aR)-3-n-hexyloxy-12-methanesulfonyl-5,6,-8a,9,10,11,12,12a,13,13a-decahydro-8H-isoquino[2,1-g][1,6]naphthyridine hydrochloride;
(8aR,12aS,13aR)-3-hydroxy-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-dihydroxy-12-methanesulfonyl-5,-6,8a,9,10,11,12,12a,13,13a-decahydro-8H-isoquino[2,1-g][1,6]naphthyridine hydrochloride;
(8aR,12aS,13aR)-1,2-dimethoxy-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-diethoxy-12-methanesulfonyl-5,6,8a,9,10,11,12,12a,13,13a-decahydro-8H-isoquino[2,1-g][1,6]naphthyridine hydrochloride;
(8aR,12aS,13aR)-2,3-di-n-butoxy-12-methanesulfonyl-5,6,8a,9,10,11,12,12a,13,13a-decahydro-8H-isoquino[2,1-g][1,6]naphthyridine hydrochloride;
(8aR,12aS,13aR)-3,4-methylenedioxy-12-methanesulfonyl-5,6,8a,9,10,11,12,12a,13,13a-decahydro-8H-isoquino[2,1-g][1,6]naphthyridine hydrochloride;
(8aR,12aS,13aR)-2-chloro-12-methanesulfonyl-5,6,8a,9,10,11,12,12a,13,13a-decahydro-8H-isoquino[2,1-g][1,6]naphthyridine hydrochloride;
(8aR,12aS,13aR)-3-chloro-12-methanesulfonyl-5,6,8a,-9,10,11,12,12a,13,13a-decahydro-8H-isoquino[2,1-g][1,6]naphthyridine hydrochloride;
(8aR,12aS,13aR)-2-fluoro-12-methanesulfonyl-5,6,8a,9,10,11,12,12a,13,13a-decahydro-8H-isoquino[2,1-g][1,6]naphthyridine hydrochloride;
(8aR,12aS,13aR)-3-fluoro-12-methanesulfonyl-5,6,8a,9,10,11,12,12a,13,13a-decahydro-8H-isoquino[2,1-g][1,6]naphthyridine hydrochloride;
(8aR,12aS,13aR)-12-aminosulfonyl-5,6,8a,9,10,11,12,-12a,13,13a-decahydro-8H-isoquino[2,1-g][1,6]naphthyridine hydrochloride;
(8aR,12aS,13aR)-3-methoxy-12-aminosulfonyl-5,6,8a,9,10,11,12,12a,13,13a-decahydro-8H-isoquino[2,1-g][1,6]naphthyridine hydrochloride;
(8aR,12aS,13aR)-12-methylaminosulfonyl-5,6,8a,9,10,11,12,12a,13,13a-decahydro-8H-isoquino[2,1-g][1,6]naphthyridine hydrochloride;
(8aR,12aS,13aR)-12-diethylaminosulfonyl-5,6,8a,9,10,11,12,12a,13,13a-decahydro-8H-isoquino[2,1-g][1,6]naphthyridine hydrochloride;
(8aR,12aS,13aR)-12-di-n-hexylaminosulfonyl-5,6,8a,9,10,11,12,12a,13,13a-decahydro-8H-isoquino[2,1-g][1,6]naphthyridine hydrochloride;
(8aR,12aS,13aR)-12-(1-piperazinosulfonyl)-5,6,8a,9,10,11,12,12a,13,13a-decahydro-8H-isoquino[2,1-g][1,6]naphthyridine hydrochloride;
(8aR,12aS,13aR)-12-(1-morpholinosulfonyl)-5,6,8a,9,10,11,12,12a,13,13a-decahydro-8H-isoquino[2,1-g][1,6]naphthyridine hydrochloride;
(8aR,12aS,13aR)-12-(1-piperidinosulfonyl)-5,6,8a,9,10,11,12,12a,13,13a-decahydro-8H-isoquino[2,1-g][1,6]naphthyridine hydrochloride;
(8aR,12aS,13aR)-3-methyl-12-ethanesulfonyl-5,6,8a,9,10,11,12,12a,13,13a-decahydro-8H-isoquino[2,1-g][1,6]naphthyridine hydrochloride;
(8aR,12aS,13aR)-3-ethoxy-12-ethanesulfonyl-5,6,8a,9,10,11,12,12a,13,13a-decahydro-8H-isoquino[2,1-g][1,6]naphthyridine hydrochloride;
(8aR,12aS,13aR)-3-n-hexyloxy-12-ethanesulfonyl-5,6,8a,9,10,11,12,12a,13,13a-decahydro-8H-isoquino[2,1-g][1,6]naphthyridine hydrochloride;
(8aR,12aS,13aR)-2,3-diethoxy-12-ethanesulfonyl-5,6,8a,9,10,11,12,12a,13,13a-decahydro-8H-isoquino[2,1-g][1,6]naphthyridine hydrochloride;
(8aR,12aS,13aR)-3-methyl-12-(1-n-hexanesulfonyl)-5,6,8a,9,10,11,12,12a,13,13a-decahydro-8H-isoquino[2,1-g][1,6]naphthyridine hydrochloride;
(8aR,12aS,13aR)-3-methoxy-12-(1-n-hexanesulfonyl)-5,6,8a,9,10,11,12,12a,13,13a-decahydro-8H-isoquino[2,1-g][1,6]naphthyridine hydrochloride;
(8aR,12aS,13aR)-2,3-dimethoxy-12-(1-n-hexanesulfonyl)-5,6,8a,9,10,11,12,12a,13,13a-decahydro-8H-isoquino[2,1-g][1,6]naphthyridine hydrochloride;

(8aR,12aS,13aR)-3-methoxy-12-phenylsulfonyl-
5,6,8a,9,10,11,12,12a,13,13a-decahydro-8H-
isoquino[2,1-g][1,6]naphthyridine hydrochloride;
(8aR,12aS,13aR)-3-methoxy-12-(N,N-dime-
thylaminosulfonyl)-5,6,8a,9,10,11,12,12a,13,13a-
decahydro-8H-isoquino[2,1-g][1,6]naphthyridine hydrochloride;
(8aR,12aS,13aR)-3-methoxy-12-(t-butylaminosulfonyl)-
5,6,8a,9,10,11,12,12a,13,13a-decahydro-8H-
isoquino[2,1-g][1,6]naphthyridine hydrochloride;
(8aR,12aS,13aR)-2,3-dimethoxy-12-(N,N-dime-
thylaminosulfonyl)-5,6,8a,9,10,11,12,12a,13,13a-
decahydro-8H-isoquino[2,1-g][1,6]naphthyridine hydrochloride;
(8aR,12aS,13aR)-2,3-methylenedioxy-12-(N,N-dime-
thylaminosulfonyl)-5,6,8a,9,10,11,12,12a,13,13a-
dechydro-8H-isoquino[2,1-g][1,6]naphthyridine hydrochloride; and
(8aR,12aS,13aR)-2-methyl-12-(2-methoxymethanesul-
fonyl)-5,6,8a,9,10,11,12,12a,13,13a-decahydro-8H-
isoquino[2,1-g][1,6]naphthyridine hydrochloride.

EXAMPLE 1A

Alternative Preparation of
(8aR,12aS,12aS)-3-methoxy-12-Methanesulfonyl-
5,6,8aα,9,10,11,12,12aα,13,13aα-decahydro-8H-
isoquino[2,1g][1,6]naphthyridine hydrochloride and
Related Compounds of Formula (1)

A. A solution of 1.45 g of (8aR,12aS,13aR)-3-methoxy-12-methanesulfonyl-5,6,8aβ,9,10,11,12,-12aβ,13,13aα-decahydro-8H-isoquino]2,1-g][1,6]naphthyridine (a compound of formula (2)) was dissolved in 50 ml of chloroform, cooled to 0° C. and 0.825 g of 80% m-chloroperbenzoic acid added. The solution was allowed to warm to room temperature, and a further 200 mg of m-chloroperbenzoic acid added. The mixture was then recooled to 0° C. and 3.2 ml of trifluoroacetic anhydride added, and the solution stirred for 20 minutes. The solution was allowed to warm to room temperature, stirred for 20 minutes, then the solvent removed under reduced pressure at room temperature. The residue was dissolved in 50 ml of ethanol, cooled to 0° C. and sodium borohydride slowly added until the solution was basic. Solvent was removed under reduced pressure and the residue partitioned between ethyl acetate and dilute hydrochloric acid. The aqueous solution was separated and basified with ammonium hydroxide, then extracted three times with methylene chloride. Solvent was removed from the combined extracts and the residue chromatographed on silica gel, eluting with ethyl acetate, giving 780 mg of (8aR,12aS,13aS)-3-methoxy-12-methanesulfonyl-5,6,8a,9,10,11,12,12a,13,-13a-decahydro-8H-isoquino[2,1-g][1,6]naphthyridine, mp 165°-166° C., $[\alpha]_D^{25} = -55.5$ (CHCl$_3$).

B. Alternatively, the conversion of a compound of formula (2) to a compound of formula (1) may be accomplished by the following procedure.

A mixture of 1.14 g of (8aR,12aS,13aR)-3-methoxy-12-methanesulfonyl-5,6,8aβ,9,10,11,12,12aβ,13,13aα-decahydro-8H-isoquino[2,1-g][1,6]naphthyridine (a compound of formula (2)) and 4.53 g of mercuric acetate in 20 ml of acetic acid and 2 ml of water is stirred at 105° C. for 1 hour. The mixture is filtered and hydrogen sulfide is bubbled through the filtrate for 5 minutes. The mixture is filtered again and the filtrate is concentrated under reduced pressure. Ethanol (50 ml) is added and the resulting solution is cooled to −20° C. and treated with 0.5 g of soduim borohydride. The solution is allowed to warm to room temperature and acidified with aqueous HCl. After washing with ethyl acetate, the aqueous layer is basified with NH$_4$OH and extracted with ethyl acetate. The ethyl acetate is washed with brine, dried over anhydrous sodium sulfate and evaporated. Chromatography of the residue on silica gel, eluting with 1% methanol in methylene chloride, affords (8aR,12aS,13aS)-3-methoxy-12-methanesulfonyl-5,6,8a,9,10,11,12,12a,13,13a-decahydro-8H-isoquino[2,1-g][1,6]naphthyridine.

C. Similarly, replacing (8aR,12aS,13aR)-3-methoxy-12-methanesulfonyl-5,6,8aβ,9,10,11,12,12aβ,13,13aα-decahydro-8H-isoquino[2,1-g][1,6]naphthyridine with other compounds of formula (2) and following the procedure of paragraph A or B above, the following compounds of formula (1) are prepared:
(8aR,12aS,13aS)-12-methanesulfonyl-5,6,8a,9,10,11,12,-12a,13,13a-decahydro-8H-isoquino[2,1-g][1,6]naphthyridine hydrochloride;
(8aR,12aS,13aS)-12-ethanesulfonyl-
5,6,8a,9,10,11,12,12,12a,13,13a-decahydro-8H-
isoquino[2,1-g][1,6]naphthyridine hydrochloride;
(8aR,12aS,13aS)-12-(1-propanesulfonyl)-
5,6,8a,9,10,11,12,12a,13,13a-decahydro-8H-
isoquino[2,1-g][1,6]naphthyridine hydrochloride;
(8aR,12aS,13aS)-12-(1-butanesulfonyl)-
5,6,8a,9,10,11,12,12a,13,13a-decahydro-8H-
isoquino[2,1-g][1,6]naphthyridine hydrochloride;
(8aR,12aS,13aS)-12-(2-methylpropanesulfonyl)-
5,6,8a,9,10,11,12,12a,13,13a-decahydro-8H-
isoquino[2,1-g][1,6]naphthyridine hydrochloride;
(8aR,12aS,13aS)-12-phenylsulfonyl-5,6,8a,9,10,11,12,-12a,13,13a-decahydro-8H-isoquino[2,1-g][1,6]naphthyridine hydrochloride;
(8aR,12aS,13aS)-12-(4-methoxyphenylsulfonyl)-
5,6,8a,9,10,11,12,12a,13,13a-decahydro-8H-
isoquino[2,1-g][1,6]naphthyridine hydrochloride;
(8aR,12aS,13aS)-12-(4-chlorophenylsulfonyl)-
5,6,8a,9,10,11,12,12a,13,13a-decahydro-8H-
isoquino[2,1-g][1,6]naphthyridine hydrochloride;
(8aR,12aS,13aS)-12-(4-fluorophenylsulfonyl)-
5,6,8a,9,10,11,12,12a,13,13a-decahydro-8H-
isoquino[2,1-g][1,6]naphthyridine hydrochloride;
(8aR,12aS,13aS)-12-(2-methoxyethanesulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-ethanesulfonyl-
5,6,8a,9,10,11,12,12a,13,13a-decahydro-8H-
isoquino[2,1-g][1,6]naphthyridine hydrochloride;
(8aR,12aS,13aS)-3-methoxy-12-(1-propanesulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-phenylsulfonyl-
5,6,8a,9,10,11,12,12a,13,13a-decahydro-8H-
isoquino[2,1-g][1,6]naphthyridine hydrochloride;
(8aR,12aS,13aS)-3-methoxy-12-(2-methylpropanesul-
fonyl)-5,6,8a,9,10,11,12,12a,13,13-decahydro-8H-
isoquino[2,1-g][1,6]naphthyridine hydrochloride;
(8aR,12aS,13aS)-3-methoxy-12-(1-piperazinosulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-(1-morpholinosulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-(1-piperidinosulfonyl)-
5,6,8a,9,10,11,12,12a,13,13a-decahydro-8H-
isoquino[2,1-g][1,6]naphthyridine hydrochloride;

(8aR,12aS,13aS)-2,3-dimethoxy-12-methanesulfonyl-5,6,8a,9,10,11,12,12a,13,13a-decahydro-8H-isoquino[2,1-g][1,6]naphthyridine hydrochloride;

(8aR,12aS,12aS)-1,4-dimethoxy-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-dimethoxy-12-(2-methyl-propanesulfonyl)-5,6,8a,9,10,11,12,12a,13,13a-decahydro-8H-isoquino[2,1-g][1,6]naphthyridine hydrochloride;

(8aR,12aS,13aS)-2,3-methylenedioxy-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-(ethylene-1,2-dioxy)-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-methylenedioxy-12-(2-methyl-propanesulfonyl)-5,6,8a,9,10,11,12,12a13,13a-decahydro-8H-isoquino[2,1-g][1,6]naphthyridine hydrochloride;

(8aR,12aS,13aS)-3-methoxy-12-(2-methoxyethanesulfonyl)-5,6,8a,9,10,11,12,12a,13,13a-decahydro-8H-isoquino[2,1-g][1,6]naphthyridine hydrochloride;

(8aR,12aS,13aS)-12-(4-aminophenylsulfonyl)-5,6,8a,9,10,11,12,12a13,13a-decahydro-8H-isoquino[2,1-g][1,6]naphthyridine hydrochloride;

(8aR,12aS,13aS)-12-(2-hydroxyethanesulfonyl)-5,6,8a,9,10,11,12,12a,13,13a-decahydro-8H-isoquino[2,1-g][1,6]naphthyridine hydrochloride;

(8aR,12aS,13aS)-1-methyl-12-methanesulfonyl-5,6,8a,9,10,11,12,12a,13,13a-decahydro-8H-isoquino[2,1-g][1,6]naphthyridine hydrochloride;

(8aR,12aS,13aS)-2-methyl-12-methanesulfonyl-5,6,8a,9,10,11,12,12a,13,13a-decahydro-8H-isoquino[2,1-g][1,6]naphthyridine hydrochloride;

(8aR,12aS,13aS)-3-methyl-12-methanesulfonyl-5,6,8a,9,10,11,12,12a,13,13a-decahydro-8H-isoquino[2,1-g][1,6]naphthyridine hydrochloride;

(8aR,12aS,13aS)-3-ethyl-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-dimethyl-12-methanesulfonyl-5,6,8a,9,10,11,12,12a,13,13a-decahydro-8H-isoquino[2,1-g][1,6]naphthyridine hydrochloride;

(8aR,12aS,13aS)-3-isobutyl-12-methanesulfonyl-5,6,8a,9,10,11,12,12a,13,13a-decahydro-8H-isoquino[2,1-g][1,6]naphthyridine hydrochloride;

(8aR,12aS,13aS)-2-n-hexyl-12-methanesulfonyl-5,6,8a,9,10,11,12,12a,13,13a-decahydro-8H-isoquino[2,1-g][1,6]naphthyridine hydrochloride;

(8aR,12aS,13aS)-3-methoxy-2-methyl-12-methanesulfonyl-5,6,8a,9,10,11,12,12a,13,13a-decahydro-8H-isoquino[2,1-g][1,6]naphthyridine hydrochloride;

(8aR,12aS,13aS)-1-methoxy-12-methanesulfonyl-5,6,8a,9,10,11,12,12a,13,13a-decahydro-8H-isoquino[2,1-g][1,6]naphthyridine hydrochloride;

(8aR,12aS,13aS)-2-methoxy-12-methanesulfonyl-5,6,8a,9,10,11,12,12a,13,13a-decahydro-8H-isoquino[2,1-g][1,6]naphthyridine hydrochloride;

(8aR,12aS,13aS)-4-methoxy-12-methanesulfonyl-5,6,8a,9,10,11,12,12a,13,13a-decahydro-8H-isoquino[2,1-g][1,6]naphthyridine hydrochloride;

(8aR,12aS,13aS)-3-ethoxy-12-methanesulfonyl-5,6,8a,9,10,11,12,12a,13,13a-decahydro-8H-isoquino[2,1-g][1,6]naphthyridine hydrochloride;

(8aR,12aS,13aS)-3-ethoxy-12-ethanesulfonyl-5,6,8a,9,10,11,12,12a,13,13a-decahydro-8H-isoquino[2,1-g][1,6]naphthyridine hydrochloride;

(8aR,12aS,13aS)-3-isopropoxy-12-methanesulfonyl-5,6,8a,9,10,11,12,12a,13,13a-decahydro-8H-isoquino[2,1-g][1,6]naphthyridine hydrochloride;

(8aR,12aS,13aS)-3-isobutoxy-12-methanesulfonyl-5,6,8a,9,10,11,12,12a,13,13a-decahydro-8H-isoquino[2,1-g][1,6]naphthyridine hydrochloride;

(8aR,12aS,13aS)-3-n-hexyloxy-12-methanesulfonyl-5,6,8a,9,10,11,12,12a,13,13a-decahydro-8H-isoquino[2,1-g][1,6]naphthyridine hydrochloride;

(8aR,12aS,13aS)-3-hydroxy-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-dihydroxy-12-methanesulfonyl-5,6,8a,9,10,11,12,12a,13,13a-decahydro-8H-isoquino[2,1-g][1,6]naphthyridine hydrochloride;

(8aR,12aS,13aS)-1,2-dimethoxy-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-diethoxy-12-methanesulfonyl-5,6,8a,9,10,11,12,12a,13,13a-decahydro-8H-isoquino[2,1-g][1,6]naphthyridine hydrochloride;

(8aR,12aS,13aS)-2,3-di-n-butoxy-12-methanesulfonyl-5,6,8a,9,10,11,12,12a,13,13a-decahydro-8H-isoquino[2,1-g][1,6]naphthyridine hydrochloride;

(8aR,12aS,13aS)-3,4-methylenedioxy-12-methanesulfonyl-5,6,8a,9,10,11,12,12a,13,13a-decahydro-8H-isoquino[2,1-g][1,6]naphthyridine hydrochloride;

(8aR,12aS,13aS)-2-chloro-12-methanesulfonyl-5,6,8a,9,10,11,12,12a,13,13a-decahydro-8H-isoquino[2,1-g][1,6]naphthyridine hydrochloride;

(8aR,12aS,13aS)-3-chloro-12-methanesulfonyl-5,6,8a,9,10,11,12,12a,13,13a-decahydro-8H-isoquino[2,1-g][1,6]naphthyridine hydrochloride;

(8aR,12aS,13aS)-2-fluoro-12-methanesulfonyl-5,6,8a,9,10,11,12,12a,13,13a-decahydro-8H-isoquino[2,1-g][1,6]naphthyridine hydrochloride;

(8aR,12aS,13aS)-3-fluoro-12-methanesulfonyl-5,6,8a,9,10,11,12,12a,13,13a-decahydro-8H-isoquino[2,1-g][1,6]naphthyridine hydrochloride;

(8aR,12aS,13aS)-12-aminosulfonyl-5,6,8a,9,10,11,12,12a,13,13a-decahydro-8H-isoquino[2,1-g][1,6]naphthyridine hydrochloride;

(8aR,12aS,13aS)-3-methoxy-12-aminosulfonyl-5,6,8a,9,10,11,12,12a,13,13a-decahydro-8H-isoquino[2,1-g][1,6]naphthyridine hydrochloride;

(8aR,12aS,13aS)-12-methylaminosulfonyl-5,6,8a,9,10,11,12,12a,13,13a-decahydro-8H-isoquino[2,1-g][1,6]naphthyridine hydrochloride;

(8aR,12aS,13aS)-12-diethylaminosulfonyl-5,6,8a,9,10,11,12,12a,13,13a-decahydro-8H-isoquino[2,1-g][1,6]naphthyridine hydrochloride;

(8aR,12aS,13aS)-12-di-n-hexylaminosulfonyl-5,6,8a,9,10,11,12,12a,13,13a-decahydro-8H-isoquino[2,1-g][1,6]naphthyridine hydrochloride;

(8aR,12aS,13aS)-12-(1-piperazinosulfonyl)-5,6,8a,9,10,11,12,12a,13,13a-decahydro-8H-isoquino[2,1-g][1,6]naphthyridine hydrochloride;

(8aR,12aS,13aS)-12-(1-morpholinosulfonyl)-5,6,8a,9,10,11,12,12a,13,13a-decahydro-8H-isoquino[2,1-g][1,6]naphthyridine hydrochloride;

(8aR,12aS,13aS)-12-(1-piperidinosulfonyl)-5,6,8a,9,10,11,12,12a,13,13a-decahydro-8H-isoquino[2,1-g][1,6]naphthyridine hydrochloride;

(8aR,12aS,13aS)-3-methyl-12-ethanesulfonyl-
5,6,8a,9,10,11,12,12a,13,13a-decahydro-8H-
isoquino[2,1-g][1,6]naphthyridine hydrochloride;
(8aR,12aS,13aS)-3-ethoxy-12-ethanesulfonyl-
5,6,8a,9,10,11,12,12a,13,13a-decahydro-8H-
isoquino[2,1-g][1,6]naphthyridine hydrochloride;
(8aR,12aS,13aS)-3-n-hexyloxy-12-ethanesulfonyl-
5,6,8a,9,10,11,12,12a,13,13a-decahydro-8H-
isoquino[2,1-g][1,6]naphthyridine hydrochloride;
(8aR,12aS,13aS)-2,3-diethoxy-12-ethanesulfonyl-
5,6,8a,9,10,11,12,12a,13,13a-decahydro-8H-
isoquino[2,1-g][1,6]naphthyridine hydrochloride;
(8aR,12aS,13aS)-3-methyl-12-(1-n-hexanesulfonyl)-
5,6,8a,9,10,11,12,12a,13,13a-decahydro-8H-
isoquino[2,1-g][1,6]naphthyridine hydrochloride;
(8aR,12aS,13aS)-3-methoxy-12-(1-n-hexanesulfonyl)-
5,6,8a,9,10,11,12,12a,13,13a-decahydro-8H-
isoquino[2,1-g][1,6]naphthyridine hydrochloride;
(8aR,12aS,13aS)-2,3-dimethoxy-12-(1-n-hexanesulfonyl)-5,6,8a,9,10,11,12,12a,13,13a-decahydro-8H-
isoquino[2,1-g][1,6]naphthyridine hydrochloride;
(8aR,12aS,13aS)-3-methoxy-12-phenylsulfonyl-
5,6,8a,9,10,11,12,12a,13,13a-decahydro-8H-
isoquino[2,1-g][1,6]naphthyridine hydrochloride;
(8aR,12aS,13aS)-3-methoxy-12-(N,N-dimethylaminosulfonyl)-5,6,8a,9,10,11,12,12a,13,13a-decahydro-8H-isoquino[2,1-g][1,6]naphthyridine hydrochloride;
(8aR,12aS,13aS)-3-methoxy-12-(t-butylaminosulfonyl)-5,6,8a,9,10,11,12,12a,13,13a-decahydro-8H-
isoquino[2,1-g][1,6]naphthyridine hydrochloride;
(8aR,12aS,13aS)-2,3-dimethoxy-12-(N,N-dimethylaminosulfonyl)-5,6,8a,9,10,11,12,12a,13,13a-decahydro-8H-isoquino[2,1-g][1,6]naphthyridine hydrochloride;
(8aR,12aS,13aS)-2,3-methylenedioxy-12-(N,N-dimethylaminosulfonyl)-5,6,8a,9,10,11,12,12a,13,13a-decahydro-8H-isoquino[2,1-g][1,6]naphthyridine hydrochloride; and
(8aR,12aS,13aS)-2-methyl-12-(2-methoxymethanesulfonyl-5,6,8a,9,10,11,12,12a,13,13a-decahydro-8H-
isoquino[2,1-g][1,6]naphthyridine hydrochloride.

EXAMPLE 2

Conversion of
(8aR,12aS,13aS)-3-methoxy-12-methanesulfonyl-
5,6,8a,9,10,11,12,12a,13,13a-decahydro-8H-
isoquino[2,1g][1,6]naphthyridine to its hydrochloride Excess 3% hydrogen chloride in methanol is added to a solution of (8aR,12aS,13aS)-3-methoxy-12-methanesulfonyl-5,6,8a,9,10,11,12,12a,13,13a-decahydro-8H-isoquino[2,1-g][1,6]naphthyridine in 20 ml methanol. Diethyl ether is added until precipitation is complete. The product is filtered, washed with ether, air dried and recrystallized from methanol/acetone to yield (8aR,12aS,13aS)-3-methoxy-12-methanesulfonyl-5,6,8a,9,10,11,12,12a,13,13a-decahydro-8H-
isoquino[2,1-g][1,6]naphthyridine hydrochloride.

In a similar manner, all compounds of formula (1) in free base form may be converted to the acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

For example:
(8aR,12aS,13aS)-3-methoxy-12-methanesulfonyl-
5,6,8a,9,10,11,12,12a,13,13a-decahydro-8H-
isoquino[2,1-g][1,6]naphthyridine hydrobromide;
(8aR,12aS,13aS)-3-methoxy-12-methanesulfonyl-
5,6,8a,9,10,11,12,12a,13,13a-decahydro-8H-
isoquino[2,1-g][1,6]naphthyridinium sulfate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium nitrate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium phosphate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium acetate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium propionate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium glycolate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium pyruvate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium oxalate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium malate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium malonate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium succinate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium maleate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium fumarate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium tartrate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium citrate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium benzoate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium cinnamate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium mandelate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium methanesulfonate;
(8aR,12aS,13aS)-3-methoxy-12-methanesulfonyl-
5,6,8a,9,10,11,12,12a,13,13a-decahydro-8H-
isoquino[2,1-g][1,6]naphthyridinium ethanesulfonate;

(8aR,12aS,13aS)-3-methoxy-12-methanesulfonyl-5,6,8a,9,10,11,12,12a,13,13a-decahydro-8H-isoquino[2,1-g][1,6]naphthyridinium p-toluenesulfonate; and (8aR,12aS,13aS)-3-methoxy-12-methanesulfonyl-5,6,8a,9,10,11,12,12a,13,13a-decahydro-8H-isoquino[2,1-g][1,6]naphthyridinium salicylate.

EXAMPLE 3

Conversion of a salt of (8aR,12aS,13aS)-3-methoxy-12-methanesulfonyl-5,6,8a,9,10,11,12,12a,13,13a-decahydro-8H-isoquino[2,1g][1,6]naphthyridine to free base.

(8aR,12aS,13aS)-3-methoxy-12-methanesulfonyl-5,6,8a,9,10,11,12,12a,13,13a-decahydro-8H-isoquino[2,1-g][1,6]naphthyridine hydrochloride suspended in 50 ml of ethyl acetate is stirred with excess dilute aqueous potassium carbonate solution until the salt is completely dissolved. The organic layer is then separated, washed twice with water, dried over magnesium sulfate and evaporated to yield (8aR,12aS,13aS)-3-methoxy-12-methanesulfonyl-5,6,8a,9,10,11,12,12a,13,-13a-decahydro-8H-isoquino[2,1-g][1,6]naphthyridine, m.p. 165°–166° C.

In a similar manner the acid addition salts of all compounds of formula (1) may be converted to the corresponding compounds in free base form.

EXAMPLE 4

Direct interchange of acid addition salts of (8aR,12aS,13aS)-3-methoxy-12-methanesulfonyl-5,6,8a,9,10,11,12,12a,13,13a-decahydro-8H-isoquino[2,1g][1,6]naphthyridine (8aR,12aS,13aS)-3-methoxy-12-methanesulfonyl-5,6,8a,9,10,11,12,12a,13,13a-decahydro-8H-isoquino[2,1-g][1,6]naphthyridine acetate (1.0 g) is dissolved in 50 ml 5N aqueous hydrochloric acid, and the solution evaporated to dryness. The product is suspended in ethyl acetate and filtered, air dried and recrystallized from methanol/acetone to yield (8aR,-12aS,13aS)-3-methoxy-12-methanesulfonyl-5,6,8a,9,10,11,12,12a,13,13a-decahydro-8H-isoquino[2,1-g][1,6]naphthyridine hydrochloride.

In a similar manner, substituting for hydrochloric acid other acids, such as sulfuric acid, nitric acid, phosphoric acid and the like, other acid addition salts of all compounds of formula (1) are prepared.

In Examples 8 through 13 the active ingredient is (8aR,12aS,13aS)-3-methoxy-12-methanesulfonyl-5,6,8a,9,10,11,12,12a,13,13a-decahydro-8H-isoquino[2,1-g][1,6]naphthyridine hydrochloride. Other compounds of formula (1) and the pharmaceutically acceptable salts thereof may be substituted therein.

EXAMPLE 5

Composition for Oral Administration

The composition contains: % wt./wt.

|  | % wt./wt. |
| --- | --- |
| Active ingredient | 20% |
| Lactose | 80% |

The two ingredients are milled, mixed and dispensed into capsules containing 100 mg each; one capsule would approximate a total daily dosage.

EXAMPLE 6

Composition for Oral Administration

The composition contains: % wt./wt.

|  | % wt./wt. |
| --- | --- |
| Active ingredient | 20.0% |
| Magnesium stearate | 0.9% |
| Starch | 8.6% |
| Lactose | 79.6% |
| PVP (polyvinylpyrrolidine) | 0.9% |

The above ingredients are combined and granulated using methanol as solvent. The formulation is then dried and formed into tablets (containing 20 mg of active compound) with an appropriate tableting machine.

EXAMPLE 7

Parenteral Formulation (IV)

The composition contains: % wt./wt.

|  | % wt./wt. |
| --- | --- |
| Active ingredient | 0.25 g |
| Propylene glycol | 20. g |
| Polyethylene glycol 400 | 20. g |
| Polysorbate 80 | 1. g |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 8

Suppository Formulation

The composition contains: % wt./wt.

|  | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 9

Topical Formulation

| Ingredients | | grams |
| --- | --- | --- |
| Active compound | | 0.2–2 |
| Span 60 | | 2 |
| Tween 60 | | 2 |
| Mineral oil | | 5 |
| Petrolatum | | 10 |
| Methyl paraben | | 0.15 |
| Propyl paraben | | 0.05 |
| BHA (butylated hydroxy anisole) | | 0.01 |
| Water | q.s | 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 10

Composition for Topical Administration to the Eye

The composition contains: % wt/vol

|  | % wt/vol |
|---|---|
| Active ingredient | 0.10 |
| Benzalkonium chloride | 0.02 |
| EDTA | 0.01 |
| Phenylethanol | 0.25 |
| Boric acid | 1.62 |
| water qs and | to adjust pH 100 ml |

The first four ingredients are dissolved in less than the required total volume of water, and the pH adjusted to 7.4. The volume is then brought to 100 ml with additional water.

EXAMPLE 11

Assay for pre- and post-synaptic α-adrenoceptor blockade

Protocol:
(According to Caroon, J. M. et al., *J. Med. Chem.*, 1982, Vol. 25, 666.)

Contralateral, prostatic and epididymal portions of the rat isolated vas deferens were suspended in separate organ baths containing oxygenated Krebs—bicarbonate solution at 37° C. The test compound was added to the Krebs—bicarbonate solution bathing the epididymal and prostatic portions of vas deferens. The contralateral portions served as control tissues. All tissues were then allowed to equilibrate with the bathing solution for 30 minutes.

Pre-synaptic α-adrenoceptor blockade was determined using the prostatic portions of vas deferens. Following the equilibration period, dose-response curves for the inhibitory effect of xylazine on the contractile response of the vas deferens to single pulse nerve stimulation were obtained.

Post-synaptic α-adrenoceptor blockade was determined using the epididymal portions of rat vas deferens. Following the equilibration period, dose-response curves for the contractile effects of phenylephrine on the vas deferens were obtained.

EXAMPLE 12

Determination of Platelet Aggregation Inhibition

Protocol:
Blood platelets are collected in the standard manner, and incubated in an Aggregation Module Incubator-Cuvette in the presence of either the inhibitor to be tested, or without said inhibitor as a control. The aggregation of the platelets is observed after the addition of an inducer, and the samples are evaluated for the presence of a lag period and the slope of the aggregation curve, as well as the maximum height of the aggregation curve in comparison to the control. $IC_{50}$ values i.e. the concentration of inhibitor required for 50% inhibition can be calculated from the inflection point on the appropriate dose response curve.

EXAMPLE 13

Determination of Effect on Intraocular Pressure

Protocol:
The compound to be tested is dissolved in saline, and applied topically to the eye. The intraocular pressure is measured immediately before application, and at specified time intervals thereafter, by means of a probe which measures the force necessary to flatten a small area of corneal surface, according to the method described by Moses, R. A., *Tr. Am. Acad. Opth. and Otol.*, Jan-Feb. 1962: 88–95.

EXAMPLE 14

Determinination of Effect on Rat Sexual Behavior

"Sexual Behaviour in Developing Male Rats", P. Sodersten, D. A. Dammassa and E. R. Smith, *Hormones and Behaviour*, Vol. 8, pp 320–334 (1977).

Protocol:
Sexually-naive male rats, weighing 200–250 g, were housed two to a cage in a normal light-cycle room (lights on 5.00 a.m., lights off 7.00 p.m.). The animals were grouped according to their weight after a 10 day acclimatization period, and tested on either the 12th or 13th day. The compound to be tested was administered 30 minutes before evaluating for sexual activity.

Stimulus female Sprague-Dawley rats, housed in a reverse light-cycle room (lights off 10.00 a.m., lights on 8.00 p.m.), were brought into sexual receptivity by injection with 20 μg of estradiol benzoate in 0.1 ml of sesame seed oil 48 hours prior to the test, and with 1 mg of progesterone in 0.1 ml of sesame seed oil 4–6 hours prior to the test.

Each male rat treated with the test compound was placed in an observation cage and allowed to acclimatize for 10 minutes. A stimulus female was then introduced into the cage and the behaviour of the male recorded on an Esterline Angus event recorder. The behaviour recorded was mounts, intromissions and ejaculations. Intromission latency (time from the start of the test to the first intromission), ejaculetion latency (time from the first intromission to ejaculation), and post-ejaculatory interval (time from ejaculation to the next following intromission) were also recorded. Tests were terminated if the intromission latency was longer than 15 minutes, the ejaculation latency was longer than 30 minutes, or the post-ejaculatory interval was in excess of 15 minutes.

In summary, the compounds of formula (1), administered 30 minutes before testing, significantly enhanced sexual activity in the naive male rat. This enhanced activity was measured by an increase in the behavior score.

EXAMPLE 15

| Weight-loss Stimulation Assay | |
|---|---|
| SPECIES | Charles River CD Sprague Dawley Rats. |
| COMPOUND | (8aR,12aS,13aS)-3-methoxy-12-methanesulfonyl-5,6,8a,9,10,-11,12,12a,13,13a-decahydro-8H-isoquino[2,1-g][1,6]naphthyridine hydrochloride |
| DOSE AND NUMBERS | 50 and 100 mg/kg/day, 10 males/group. |
| DURATION OF DOSING | Two weeks. |

| Weight-loss Stimulation Assay | |
|---|---|
| CONCLUSION | 50 and 100 mg/kg/day dosed rats gained 14% less bodyweight then controls. |

EXAMPLE 16

Irritable-Bowel Syndrome Assay

Protocol:

The test used is a modification of the method of Macht and Barba-Gose (Macht, D. T. and Barba-Gose, J. (1931): J. Amer. Pharm. Ass. 20, 558), which traces the transit of a charcoal meal through the intestine as an index of transit time. In the present model, intestinal transit in conscious mice (15–20 g) was accelerated with an oral dose of barium chloride (300 mg/kg) administered at the same time as the charcoal meal. The animals were sacrificed 10 min. later and the distance travelled by the charcoal measured.

The antagonist compound was given as a 15 min. oral pretreatment and its effects on barium-stimulated intestinal transit of the charcoal meal was calculated.

EXAMPLE 17

Antidepressant Assay

Protocol:

Antidepressant utility was assessed by the ability of compounds of formula (1) to down-regulate $\beta$-adrenoreceptors in rat cerebral cortex after chronic dosing; down-regulation of $\beta$-adrenoreceptors may be an index of antidepressant effectiveness (Clark, Michel and Whiting, 1986, Progress in Medicinal Chemistry, Vol. 23, 1–39). The number of $\beta$-adrenoreceptors was measured using an adaptation of the method of Bylund and Snyder (1976, Molecular Pharmacology, 12, 568) and expressed as $B_{max}$ (fmol/mg protein). Chronic dosing with a compound of formula (1) reduced the number of $\beta$-adrenoreceptors in rat cerebral cortex without changing the affinity of the receptors (Kd).

Male Sprague-Dawley rats were dosed with 0.5 mg/kg of a compound of formula (1) o.d. p.o. for 14 days. The animals were sacrificed 24 hours after the last dose.

Tris washed cortical membranes were prepared from the rat brains and incubated with [3H]-dihydroalprenolol (0.1–4.0 nM) for 30 mins. at 25° C. The incubation was terminated by rapid filtration over Whatman GF/B filters in a Brandel Cell Harvester. Bound radioactivity was defined as the amount of ligand bound in the presence of 0.5 mM isoprenaline.

EXAMPLE 18

Hypoglycaemic Assay

A compound of formula (1) was administered to groups of 10 male mice (30 mg/kg, intraperitoneally) and found to reduce blood glucose; these hypoglycaemic effects indicate potential utility as an antidiabetic agent.

EXAMPLE 19

Antihypertensive Assay

Compounds of formula (1) have antihypertensive activity in that the compound lowered blood pressure in conscious spontaneously hypertensive rats when administered intravenously. The mean blood pressure was monitored by an indwelling catheter in the tail artery.

EXAMPLE 20

Anxiolytic Assay

Protocol:

The method used was that described by Crawley and Goodwin ("Preliminary behavior model for the anxiolytic effects of benzodiazepines." Pharmac. Biochem. Behavior 1980;13:167–170.). This method involves placing native mice in a novel test environment which comprises a box divided by a partition into a dark area and a light area. Mice are allowed to shuttle between the dark and light area for a period of 10 mins. During this time the number of shuttles, total locomotor activity and total time spent in the dark were monitored. A compound of formula (1) (0.3 mg/kg) was administered ip, and the mouse behaviour observed 30 minutes later. The prescribed test parameters (number of shuttles, time spent in the dark area, and total locomotor activity) were compared to control data using a standard Student's t-test and the percent of control response was calculated.

Compounds of formula (1) displayed a profile which is generally associated with an anxiolytic agent within this model.

I claim:

1. A compound of the formula (1):

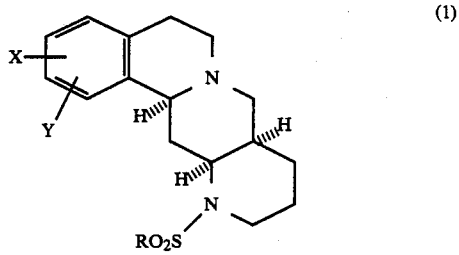

in which:

X and Y are independently hydrogen, hydroxy, lower alkyl of one to six carbon atoms, lower alkoxy of one to six carbon atoms or halo, or X and Y taken together is methylenedioxy or ethylene-1,2-dioxy; and R is lower alkyl of one to six carbon atoms, phenyl optionally substituted by one or two substituents chosen from halo or amino groups or lower alkyl or lower alkoxy groups of one to four carbon atoms, —(CH$_2$)$_m$OR$^1$ or —NR$^1$R$^2$ wherein m is an integer of 1 to 6 and R$^1$ and R$^2$ are independently hydrogen or lower alkyl, or —NR$^1$R$^2$ taken together is a heterocycle of the formula:

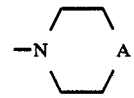

wherein A is —CH$_2$—, —NR$^1$— or oxygen; or a pharmaceutically acceptable salt thereof.

2. A compound of claim 1 in which X and Y are independently hydrogen or lower alkoxy having one to four carbon atoms, or X and Y taken together is methylenedioxy, or a pharmaceutically acceptable salt thereof.

3. A compound of claim 2 in which R is lower alkyl having one to six carbon atoms, or a pharmaceutically acceptable salt thereof.

4. A compound of claim 3 in which X and Y taken together is 2,3-methylenedioxy and R is methyl, namely (8aR,12aS,13aS)-2,3-methylenedioxy-12-methanesulfonyl-5,6,8a,9,10,11,12,12a,13,13a-decahydro-8H-isoquino[2,1-g][1,6]naphthyridine, or a pharmaceutically acceptable salt thereof.

5. A compound of claim 3 in which X and Y taken together is 2,3-methylenedioxy and R is 2-methylpropyl, namely (8aR,12aS,13aS)-2,3-methylenedioxy-12-(2-methylpropanesulfonyl)-5,6,8a,9,10,11,12,12a,13,13a-decahydro-8H-isoquino[2,1-g][1,6]naphthyridine, or a pharmaceutically acceptable salt thereof.

6. A compound of claim 3 in which X is 3-methoxy, Y is hydrogen and R is methyl, namely (8aR,12aS,13aS)-3-methoxy-12-methanesulfonyl-5,6,8a,9,10,11,12,12a,13,13a-decahydro-8H-isoquino[2,1-g][1,6]naphthyridine, or a pharmaceutically acceptable salt thereof.

7. A compound of claim 3 in which X is 3-methoxy, Y is hydrogen and R is 2-methylpropyl, namely (8aR,12aS,13aS)3-methoxy-12-(2-methylpropanesulfonyl)-5,6,8a,9,10,11,12,12a,13,13a-decahydro-8H-isoquino[2,1-g][1,6]naphthyridine, or a pharmaceutically acceptable salt thereof.

8. A compound of claim 3 in which X is 2-methoxy, Y is 3-methoxy and R is methyl, namely (8aR,12aS,13aS)-2,3-dimethoxy-12-methanesulfonyl-5,6,8a,9,10,11,12,12a,13,13a-decahydro-8H-isoquino[2,1-g][1,6]naphthyridine, or a pharmaceutically acceptable salt thereof.

9. A compound of claim 3 in which X and Y are both hydrogen and R is methyl, namely (8aR,12aS,13aS)-12-methanesulfonyl-5,6,8a,9,10,11,12,12a,13,13a-decahydro-8H-isoquino[2,1-g][1,6]naphthyridine, or a pharmaceutically acceptable salt thereof.

10. A compound of claim 3 in which X and Y are both hydrogen and R is 2-methylpropyl, namely (8aR,12aS,13aS)-12-(2-methylpropanesulfonyl)-5,6,8a,9,10,11,12,12a,13,13a-decahydro-8H-isoquino[2,1-g][1,6]naphthyridine, or a pharmaceutically acceptable salt thereof.

11. A compound of claim 2 in which R is $-NR^1R^2$, or a pharmaceutically acceptable salt thereof.

12. A compound of claim 11 in which $R^1$ and $R^2$ are independently hydrogen or lower alkyl of one to four carbon atoms, or a pharmaceutically acceptable salt thereof.

13. A compound of claim 12 in which X is 3-methoxy and Y is hydrogen, and $R^1$ and $R^2$ are both methyl, namely (8aR,12aS,13aS)-3-methoxy-12-N,N-dimethylaminosulfonyl-5,6,8a,9,10,11,12,12a,13,13a-decahydro-8H-isoquino[2,1-g][1,6]naphthyridine, or a pharmaceutically acceptable salt thereof.

14. A compound of claim 2 in which R is $-(CH_2)_mOR^1$, or a pharmaceutically acceptable salt thereof.

15. A compound of claim 14 in which m is 2 and $R^1$ is methyl, or a pharmaceutically acceptable salt thereof.

16. A compound of claim 15 in which X and Y are both hydrogen, namely (8aR,12aS,13aS)-12-(2-methoxyethanesulfonyl)-5,6,8a,9,10,11,12,12a,13,13a-decahydro-8H-isoquino[2,1-g][1,6]naphthyridine, or a pharmaceutically acceptable salt thereof.

17. A compound of claim 15 in which X is 3-methoxy and Y is hydrogen, namely (8aR,12aS,13aS)-3-methoxy-12-(2-methoxyethanesulfonyl)-5,6,8a,9,10,11,12,12a,13,13a-decahydro-8H-isoquino[2,1-g][1,6]naphthyridine, or a pharmaceutically acceptable salt thereof.

18. A composition suitable for administration to a mammal having a disease-state which is treatable with an $\alpha_2$-blocker, which composition comprises a pharmaceutically acceptable non-toxic carrier and a therapeutically effective amount of a compound of the formula

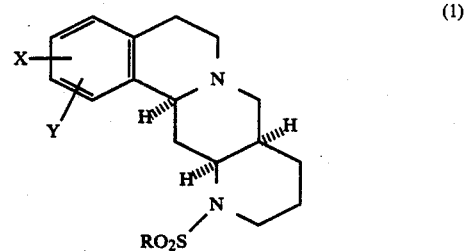

(1)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy; and
R is lower alkyl of one to six carbon atoms, phenyl optionally substituted by one or two substituents chosen from halo or amino groups or lower alkyl or lower alkoxy groups of one to four carbon atoms, $-(CH_2)_mOR^1$ or $-NR^1R^2$ wherein m is an integer of 1 to 6 and $R^1$ and $R^2$ are independently hydrogen or lower alkyl, or $-NR^1R^2$ taken together is a heterocycle of the formula:

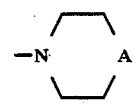

wherein A is $-CH_2-$, $-NR^1-$ or oxygen; or a pharmaceutically acceptable salt thereof, in admixture with one or more pharmaceutically acceptable carriers.

19. A method for treating a mammal having a disease-state which is treatable with an $\alpha_2$-blocker, which comprises administering a therapeutically effective amount of a compound of the formula

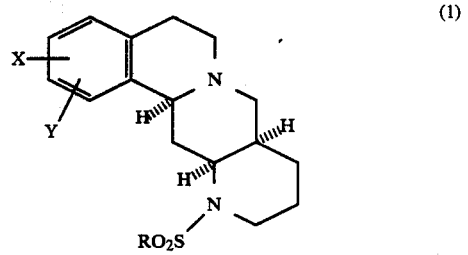

(1)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy; and
R is lower alkyl of one to six carbon atoms, phenyl optionally substituted by one or two substituents chosen from halo or amino groups or lower alkyl or lower alkoxy groups of one to four carbon atoms, —$(CH_2)_mOR^1$ or —$NR^1R^2$ wherein m is an integer of 1 to 6 and $R^1$ and $R^2$ are independently hydrogen or lower alkyl, or —$NR^1R^2$ taken together is a heterocycle of the formula:

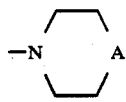

wherein A is —$CH_2$—, —$NR^1$— or oxygen; or a pharmaceutically acceptable salt thereof.

20. The method of claim 19, wherein said disease-state is selected from depression, anxiety, excessive paltelet aggregation, diabetes, male impotence, elevated intraocular pressure and irritable-bowel syndrome.

21. An intermediate of the formula

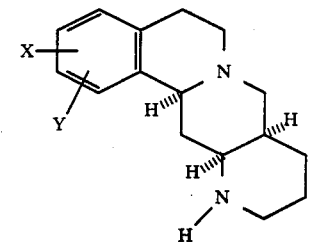
(XI)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy.

* * * * *